US009482611B2

(12) United States Patent
Dasgupta et al.

(10) Patent No.: US 9,482,611 B2
(45) Date of Patent: Nov. 1, 2016

(54) METHOD AND APPARATUS FOR SCANNING DETECTION

(71) Applicant: Board of Regents, The University of Texas System, Austin, TX (US)

(72) Inventors: Purnendu K. Dasgupta, Arlington, TX (US); Brian N. Stamos, Arlington, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 112 days.

(21) Appl. No.: 14/502,536

(22) Filed: Sep. 30, 2014

(65) Prior Publication Data
US 2015/0090013 A1    Apr. 2, 2015

Related U.S. Application Data

(60) Provisional application No. 61/884,365, filed on Sep. 30, 2013.

(51) Int. Cl.
*G01N 21/59* (2006.01)
*G01N 21/64* (2006.01)
*G01N 30/64* (2006.01)
*G01N 30/74* (2006.01)
*G01N 30/60* (2006.01)
G01N 27/447 (2006.01)

(52) U.S. Cl.
CPC .............. *G01N 21/59* (2013.01); *G01N 21/64* (2013.01); *G01N 30/6082* (2013.01); *G01N 30/64* (2013.01); *G01N 30/74* (2013.01); G01N 27/4473 (2013.01); G01N 2030/645 (2013.01)

(58) Field of Classification Search
CPC ....................................................... G01N 21/59
USPC ................................... 73/61.48, 23.4, 61.58
See application file for complete search history.

(56) References Cited

U.S. PATENT DOCUMENTS

| 5,114,551 A | 5/1992 | Hjerten et al. |
| 2004/0166588 A1 | 8/2004 | Farquharson et al. |
| 2012/0160691 A1 | 6/2012 | Mahabadi et al. |

FOREIGN PATENT DOCUMENTS

| EP | 1 004 025 B1 | 1/2004 |
| JP | 58-45552 A | 3/1983 |

OTHER PUBLICATIONS

Stephen C. Beale, et al., "Spatial-Scanning Laser Fluorescence Detection for Capillary Electrophoresis", Anal. Chem. 1995, 67, 3367-3371.

(Continued)

*Primary Examiner* — Laura Martin
*Assistant Examiner* — Jean Morello
(74) *Attorney, Agent, or Firm* — Morgan, Lewis & Bockius LLP

(57) ABSTRACT

An apparatus for scanning and detecting analytes in real time as they move through a separation conduit is provided. The apparatus may include a detector mounted on a scanner containing a separation conduit positions under the scanner such that the scanner may move back and forth along the conduit, producing time and space data of the column as the analyte moves through and providing information regarding elution of the analyte in real time. A method for real time analysis of analytes as they move through a separation conduit is also provided.

29 Claims, 27 Drawing Sheets

(56) References Cited

OTHER PUBLICATIONS

E.E. Brumbaugh, et al., "Molecular Sieve Studies of Interacting Protein Systems: III. Measurement of Solute Partitioning by direct ultraviolet scanning of gel columns", J. Biol. Chem. 1968, 243:6315-6324.

Damian Connolly, et al., "The Use of Contactless Conductivity for the On-Column Characterisation and Visualisation of Packing Homogeneity and Band Broadening in Capillary LC", Chromatographia 2009, 70, Sep. (No. 5/6), 915-920.

Damian Connolly, et al., "Non-invasive characterization of stationary phases in capillary flow systems using scanning capacitively coupled contactless conductivity detection($sC^4D$)", Trends in Analytical Chemistry, vol. 29, No. 8, 2010.

Tim Dallas, et al., "Light at the end of the tunnel: recent analytical applications of liquid-core waveguides", Trends in Analytical Chemistry, vol. 23, No. 5, 2004.

Purnendu K. Dasgupta, et al., "Luminescence Detection with a Liquid Core Waveguide", Anal. Chem. 1999, 71, 1400-1407.

José A. Fracassi da Silva, et al., "An Oscillometric Detector for Capillary Electrophoresis", Anal. Chem. 1998, 70, 4339-4343.

David G. Gelderloos, et al., "Whole Column Detection Chromatography: Computer Simulations", Anal.Chem. 1986, 58, 900-903.

Eoin Gillespie, et al., "Development of a contactless conductivity detector cell for 1.6 mm O.D. (1/16th inch) HPLC tubing and micro-bore columns with on-column detection", The Royal Society of Chemistry 2008, 133, 1104-1110.

Akinde Kadjo, et al., "Tutorial: Simulating chromatography with Microsoft Exel Macros", Analytica Chimica Acta 773 (2013) 1-8.

Pavel Kuban, et al., "Contactless conductivity detection for analytical techniques: Developments form 2010 to 2012", Electrophoresis 2013, 34, 55-69.

Shu-Hui Lin, et al., "Peak crossover in high-performance liquid chromatography elution monitored using whole-column detection", Journal of Chromatography A. 1201 (2008) 128-131.

Zhen Liu, et al., "Applications of capillary isoelectric focusing with liquid-core waveguide laser-induced fluorescence whole-column imaging detection", Analytical Biochemistry 336 (2005) 94-101.

Aine Moyna, et al., "Iminodiacetic acid functionalized organopolymer monoliths: application to the separation of metal cations by capillary high-performance chelation ion chromatography", Anal Bioanal Chem (2013) 405:2207-2217.

José A. Olivares, et al., "Liquid Core Waveguide for Full Imaging of Electrophoretic Separations", Anal. Chem. 2002, 74, 2008-2013.

Jan Preisler, et al., "Characterization of Nonbonded Poly(ethylene oxide) Coating for Capillary Electrophoresis via Continuous Monitoring of Electroosmotic Flow", Anal. Chem. 1996, 68, 2885-2889.

Kathy L. Rowlen, et al., "Whole Column Detection: Application to High-Performance Liquid Chromatography", Anal. Chem. 1989, 61, 2624-2630.

Jiaqi Wu, et al., "Universal Detection for Capillary Isoelectric Focusing without Mobilization Using a Concentration Gradient Imaging System", Anal. Chem., 1992, 64, 224-227.

Jiaqi Wu, et al., "Application of capillary isoelectric focusing with absorption imaging detection to the analysis of proteins", Journal of Chromatography B, 657 (1994) 327-332.

Xing-Zheng Wu, et al. "Whole-Column-Imaging Detection for Capillary Isoelectric Focusing and Capillary Electrophoresis", LCGC, vol. 19, No. 5, May 2001.

Xing-Zheng Wu, et al. "Whole-column imaging-detection techniques and their analytical applications", Trends in Analytical Chemistry, vol. 24, No. 5, 2005.

Xiaobing Xi, et al., "Axial-Beam On-Column Absorption Detection for Open Tubular Capillary Liquid Chromatography", Anal. Chem. 1990, 62, 1580-1585.

Wang, J., et al. "Movable Contactless-Conductivity Detector for Microchip Capillary Electrophoresis", Analytical Chemistry, Sep. 1, 2003, vol. 75, No. 17, pp. 4475-4479.

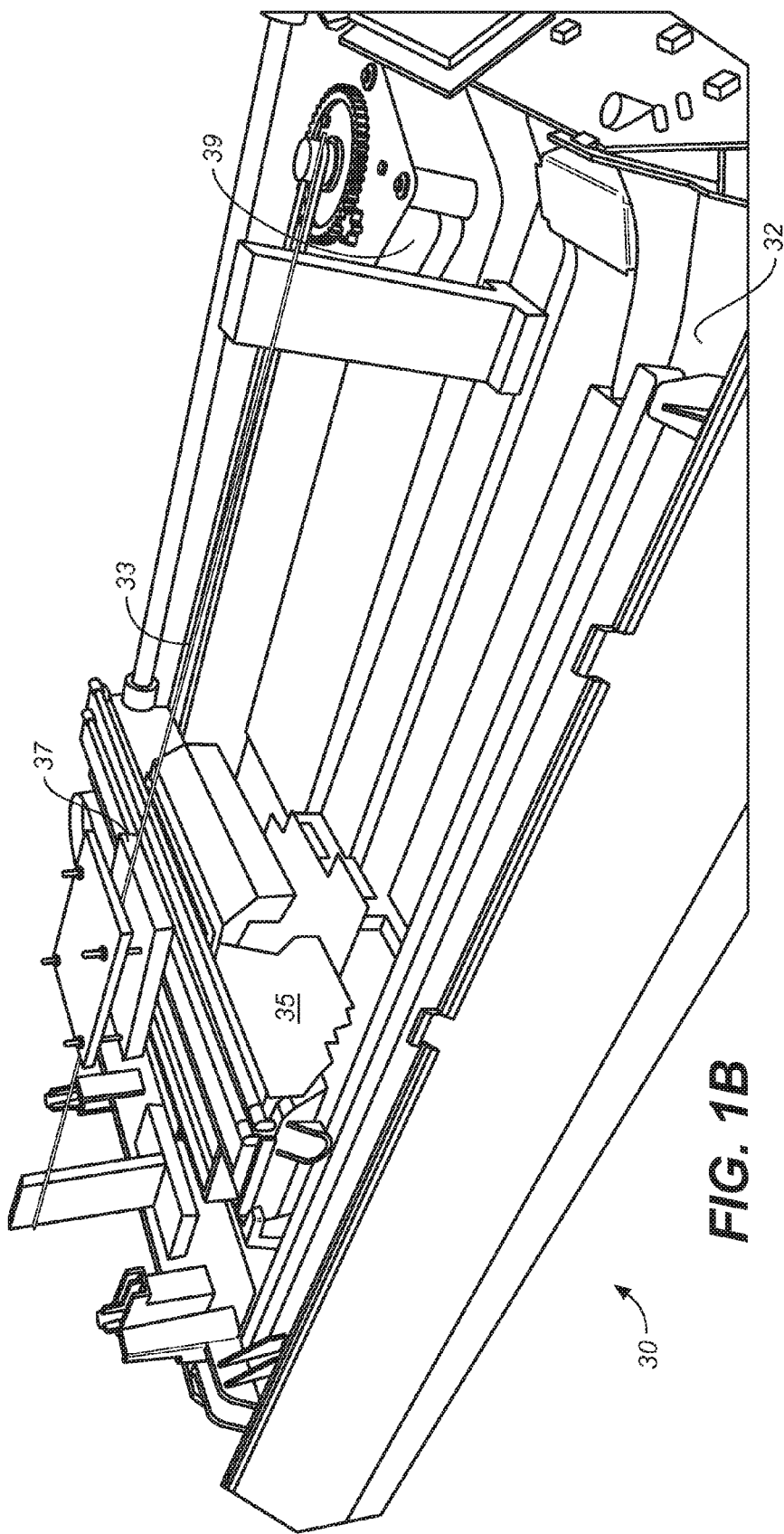

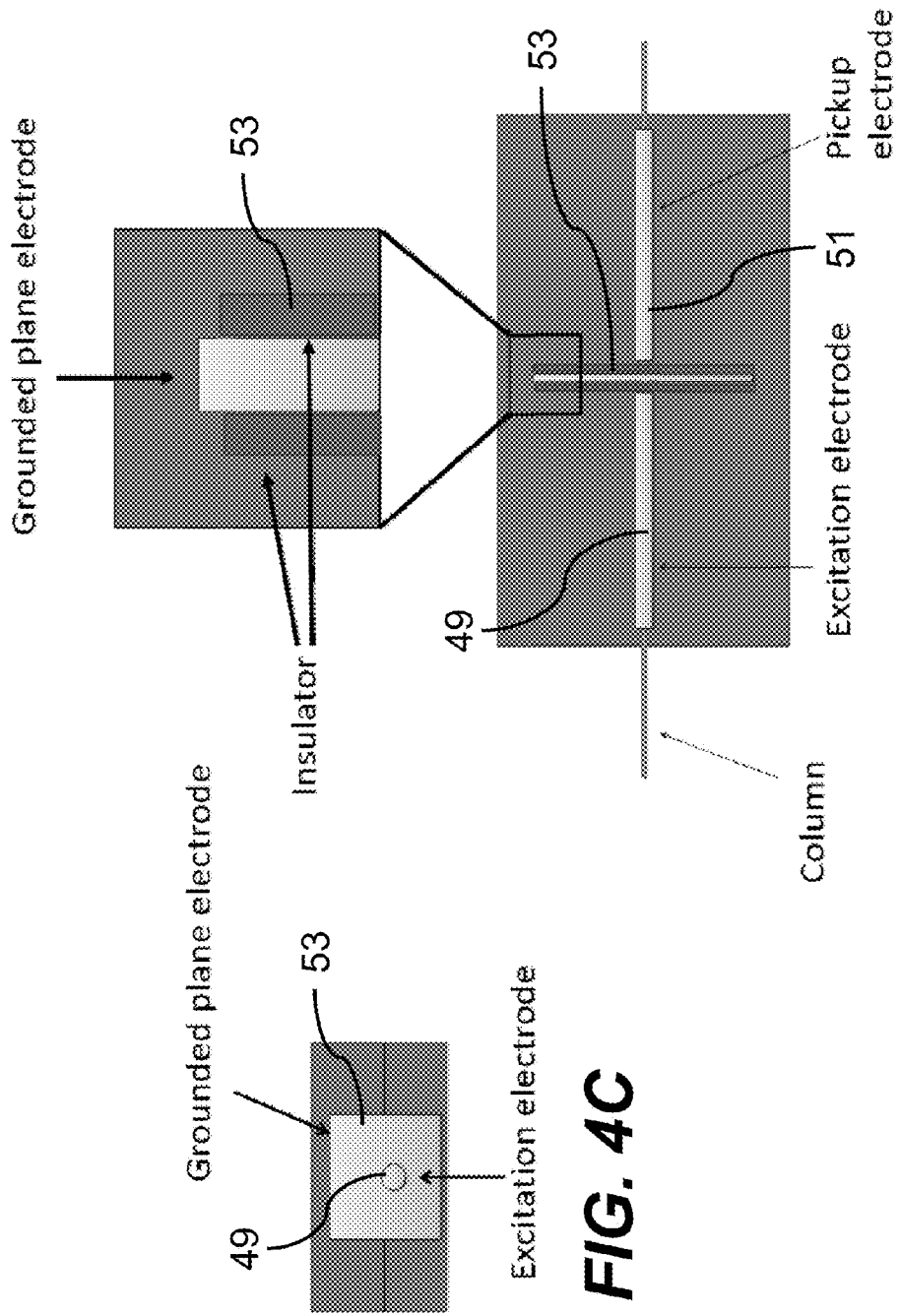

METHOD AND APPARATUS FOR SCANNING DETECTION

CROSS-REFERENCES TO RELATED APPLICATIONS

This application claims priority to U.S. Provisional Patent Application No. 61/884,365 filed Sep. 30, 2013 and entitled CONDUCTOMETRIC AND OPTICAL METHOD FOR SPACE-TIME 3D DETECTION, the entire contents of which is incorporated herein for all purposes by this reference.

STATEMENT REGARDING FEDERALLY SPONSORED RESEARCH OR DEVELOPMENT

This invention was made with government support under Grant Number NNX11A066G awarded by National Aeronautics and Space Administration. The government has certain rights in the invention.

FIELD OF THE INVENTION

The present invention relates generally to an apparatus and a method for detecting elution of analyte, or analyzing a sample moving along a chromatography column in real time. The apparatus comprises a detector movably mounted on a base for scanning back and forth along a chromatography column in order to provide real time information regarding elution of a desired analyte. A method of detecting a desired analyte using the apparatus of the invention is also provided.

BACKGROUND OF THE INVENTION

Liquid phase columnar separations are among the workhorse techniques for a present day analytical chemist. Capillary electrophoresis (CE) and especially high performance liquid chromatography (HPLC) are the two dominant examples. In either one, the sample is injected at one end of a tubular conduit and moved towards the exit of the conduit either by a pumped eluent flowing through the conduit (e.g., HPLC) or by applying an electrical field applied across the length of the tube (e.g., CE). Towards the end of the conduit (CE, capillary HPLC) or immediately after the conduit a detector is located. Separation of different constituents in the sample is achieved because they move at different rates through the column and arrive at the detector at different times.

Particularly in HPLC to achieve time-efficient separation and sensitive detection, a technique called gradient elution is used, especially when the sample contains both (a group of) weakly retained (fast moving) species and (a group of) strongly retained species. In this case, a weak eluent (low pushing power) is used during the initial phase of the separation so that separation is achieved between the different weakly retained species. Then the eluent strength is increased to elute the strongly held species and achieve separation between them. If the weak eluent is used throughout, the strongly held analytes will take a very long time to elute (if they elute at all) and the resulting peaks will be very broad, making sensitive detection difficult. If the strong eluent is used throughout, the weakly retained species will elute together as a group, undifferentiated.

There are many programs that simulate separations described above, including one recently developed by the inventors. See Reference (23) below. Such simulations and real life experiments indicate that even in isocratic (i.e., not involving a gradient), the separation of the analytes is often complete long before it reaches the terminal detector, not only time is wasted but the bands broaden over the rest of the time and detection sensitivity is decreased. In gradient elution, it is not uncommon that if the strong eluent concentration is increased too soon, a pair of weakly retained species that were separated as they resided on the column ultimately got pushed into one undifferentiated peak. Picking a particular temporal gradient program is rarely approached a priori, rather one tries to fine tune this as a result of several successive trials of varying composition.

Ironically when Mikhail Tswett first invented chromatography, he separated plant pigments on a glass column filled with $CaCO_3$ and he was able to observe his separation visually. Although admittedly he did not have any means in his time to quantitate the bands on the column. In principle, if you can not only see the separation in a qualitative manner but in a quantitative fashion with good sensitivity, there is no need to wait until an end-column detector sees the eluted band. Indeed, if one can see the separation in near real time, one can alter the elution conditions concurrently to achieve the best separation and the most sensitive quantitation possible.

The concept of quantitatively detecting/imaging what is present in different locations in the column at all times during the separation process is not new. The term "Whole Column Detection" (WCD) was coined first to the inventors' knowledge by Birks and his students in a theoretical simulation. See Reference (1) below. In traditional chromatography with a terminal post-separation detection arrangement, the only identifying marker of an analyte independent of any specific detector is the terminal retention time, often described in terms of its "retention factor". Note that spectral characteristics and such others that are sometimes used for identification are not intrinsic to chromatography, that information is detector specific.

Obviously to perform whole column detection, the detector must be able to "see through" the bounding walls of the column. As early as 1968, Brumbaugh and Ackers described "scanning gel chromatography" where the column was moved past a fixed light source-detector configuration and were able to monitor the absorbance profile of molecular sieve separations throughout the length of a gel column. See Reference (2) below. Previously, moving a HPLC column (to which today pumps and an injector are integrally attached) is not very practical. In their first experimental paper, Birks and his students used a metal jacketed glass column, a long fluorescent lamp emitting at 365 nm on one sides and 14 pairs of holes opposite each other in the metal jacket: light entered on one side and was detected with 14 individual photodiodes on the other side. See Reference (3) below.

While a number of the theoretical predictions and an elucidation of how retention factors change under gradient conditions could be verified and demonstrated, with a maximum resolution of 14 points along the column, performance and accuracy of the results were less than desirable.

Pawliszyn used his considerable prior experience in detecting refractive index changes in a capillary to design a refractive index gradient detection system over an effective length of 15 mm in a capillary isoelectric focusing (CIEF) analysis system. See Reference (4) below. A stationary focused He—Ne laser source was used. The beam was expanded by a lens after the capillary such that the distance on the capillary was magnified 10 times in the detector plane where the scanned distance was 150 mm with a resolution of 0.1 mm (a syringe pump drive was adapted) providing a 1500 point resolution over the entire separation distance of 15 mm. Because it was not possible to move the single detector photodiode at sufficient speeds needed for fast electrophoretic separations, they also imaged a smaller (3 mm) length of the separation capillary with a 128 element photodiode array. A wider photodiode array would have allowed a longer portion of the separation capillary to be directly imaged and the moving photodetector can be dispensed with. Precisely this was done in 1994 with an argon ion laser source and a 1024—element CCD detector—the 25 mm wide detector imaged 25 mm of the capillary (with the resolution obviously being 1024 points). See Reference (5) below; see also U.S. Pat. No. 5,395,502.

The same concept as above was adapted by Beale and Sudmeier in 1995 to CE or CIEF with laser-induced fluorescence (LIF) detection. See Reference (6) below. They placed the entire separation capillary on a motorized translation stage (max speed 50 mm/s), up to 19 cm length could be brought under the field of view of a microscope objective. The LIF system operated in the confocal mode. They obtained better results with conventional capillaries from which the polyimide coating was removed (with either fuming sulfuric acid or a butane torch) than a silica capillary with UV-transparent coating. They noted that with inner bores <75 µm, it becomes very difficult to maintain laser focus inside the capillary, which greatly decreases signal-to-noise (S/N).

It is also to be noted that few substances have native fluorescence. Any analysis system relying on LIF must undergo prior derivatization. No suitable derivatization chemistry may exist; at the very least this represents an extra cumbersome step. Photobleaching of fluorescence with repeated scanning is also a problem, especially with an intense source.

In 1996, Preisler and Yeung illuminated 232 mm of a capillary with an Ar laser and a plano-convex lens. See Reference (7) below. The entire illuminated area was monitored through a perpendicularly mounted 578 element CCD array equipped with an appropriate emission filter.

They merely monitored the movement of a fluorescein band/front to determine flow velocity but in principle this will allow monitoring the separation of analytes that can be made to fluoresce with the particular laser source with the caveats already outlined. Prior to this in 1994 an arrangement was demonstrated by Wu and Pawliszyn where the input light was coupled by a fiber-optic array to the capillary but the sensitivity was poor as the light coupling was not efficient. See Reference (4) below.

In 1998 based on Pawilszyn's work, Convergent Biosciences in Canada commercialized an imaging CIEF detection system that uses a fiber optic array to bring in 280 nm UV light from a Xenon lamp into a capillary cassette with a 50 µm wide 5 cm long aperture.

The transmitted light is read by a CCD array. This instrument (iCE280) is still sold as such and as part of a more elaborate iCE3 system.

In 2001 in their review of imaging detection in CE and CIEF, Wu et al. summarized the status of the field at that time. See Reference (8) below. The favored generic arrangement of illumination and detection, whether by transmittance or fluorescence, is shown in the article; the iCE280 arrangement does fall in this category.

It is believed that the iCE280 is thus far the only commercial instrument to offer whole column or imaging detection and it is ideally suited only when the total separation distance is small, e.g., 5 cm for the iCE280. This is applicable in CIEF but there are few other techniques where this can be accepted.

A wholly different approach is possible with a liquid core waveguide (LCW) both for absorbance and fluorescence detection. An LCW is a tube or conduit where the wall is composed of a material that is both optically transparent in the wavelength region of interest.

Light can proceed through a long LCW capillary with relatively small loss. If such a capillary is axially illuminated and the light passing through the entire length of the capillary is monitored, as soon as the sample is injected light transmission goes down due to the light absorbing components present in the sample. The signal will remain unaltered until the earliest eluting component falls off the detection path—the transmitted light will rise by that amount. If this data is depicted as absorbances vs. time, the output will resemble a downward stair case with the transition from each step to another depicting the elution of an analyte. A more conventional chromatogram or electropherogram can be obtained by differentiating the signal with time.

Although this concept was demonstrated with regular capillaries (which lose a lot more light, see Reference 9 below), the process becomes more practical with a LCW capillary (see Reference 10 below). Nevertheless, this system has numerous difficulties. Even though a large absorbing peak may be completely separated, they appear in the signal together. If the small one elutes first its quantitation accuracy is limited by the need to subtract one large number from another. Differentiation magnifies noise. Much of the time detection is done with a number of absorbing components in the light path this reduces light throughput and increases detector noise.

Fluorescence detection with a liquid core waveguide tube has more possibilities. If the excitation light is radially incident on the capillary, the unabsorbed incident radiation largely passes out through the wall. In contrast, a significant portion of the emitted fluorescent light proceeds down the tube where it can be picked up either by a fiber optic coupled to a photodetector or directly by a photodetector. See References (11) and (12) below.

Instead of trying to illuminate the tube uniformly along its length, a laser beam can be scanned (either through space or coupled by a fiber optic) along the separation capillary, revealing where the fluorescently labeled analytes are located. In 2002, Olivares et al. described such a system and used it for both CE and CIEF over a scanning length of 12 cm. See Reference (13) below.

There are some complications with such an arrangement, aside from the general problems with fluorescence detection already mentioned. Except when the analyte is the nearest one the detector, any fluorescence elicited and traveling to the detector must travel through other analyte band(s) between it and the detector and light will be lost by absorption making quantitation complicated.

The roles of the axial and radial light can be reversed. The LCW can be illuminated axially and the fluorescence radiation exiting the wall can be read by an imaging detector/camera. See Reference (14) below. Other applications of this configuration were discussed by the senior author in a 2005 review. See Reference (15) below. However, this configuration has even more problems than the one just discussed from axial light loss due to absorption by preceding analyte zones and accurate quantitation is difficult. This was described in U.S. Pat. No. 6,852,206 but for reasons above, never commercialized.

An approach that is similar to Wu and Pawliszyn's 1992 paper (see Reference (4) below) in that the column was uniformly illuminated along its length and the detector (in this case a CCD array, rather than a photodiode), registering a portion of the column was moved along (in this case by an optical scanner drive, rather than a syringe pump drive) was described by Lin et al in 2008. See Reference (16) below. They used however not an open tubular capillary but a 3 mm ID glass tube with 10 µm octadecylsilane bonded silica particles. This was then inserted into a stainless steel tube with windows on opposite sides cut in it. The authors stated that the system permitted a resolution of 0.3 mm. As with the apparatus described in Reference (4), light coupling in and out of the column was through space.

It is important to note that that during gradient elution the analyte does not move at a constant speed throughout: the entire journey of an analyte—the two dimensional space-time transit map of the analyte, as it were—can serve as a much more specific and discriminating marker rather than a one dimensional specification of when a given analyte "finished the race".

Currently, detection for chromatography is done in a fixed position, typically after elution from the column. This means that not only must one wait for a period of time for all of the analytes to elute, but also that the time used to perform the separation is inefficient. This is due to the fact that, though a separation may be complete in the first 10% of the column, it is unknown until it reaches the detector. Additionally, if a gradient elution method is used, it is possible to have separated analytes before the increase in eluent strength, but have them co-elute when stronger eluents are applied.

What is needed is a system for detecting the elution of analyte along a separation conduit in real time, allowing for more efficient separation and detection of analytes in a given sample.

BRIEF SUMMARY

The present invention provides a system for real time detection of analytes as they move along a separation conduit. The separation conduit may be a packed column or an open tubular column. The detection method may be conductometric (conductance or admittance), optical detection (absorbance or fluorescence), or a combination thereof. The detector is in intimate contact with the separation conduit and is moved back and forth repeatedly along the conduit, providing real time scans of the sample moving along the conduit. A high precision stepper motor drive may be used to move the detector back and forth along the conduit. The repeated scans provide a real time view of the analytes moving through the conduit.

One aspect of the present invention is directed to an apparatus for real time detection of elution of one or more analytes, the apparatus including: a separation conduit an integrated detector including an excitation source and a sensor, both located immediately adjacent to the separation conduit, wherein the integrated detector is configured to move along a length of the separation conduit and a driver moving the integrated detector along the length of the separation conduit, wherein the integrated detector scans the separation conduit and detects analyte as it moves through the separation conduit.

Another aspect of the present invention is directed to a method for detecting elution of one or more analytes in real time, the method including: injecting an analyte sample through a separation conduit, the analyte sample containing an analyte sample containing an analyte within an eluent or background electrolyte; and repeatedly scanning the analyte sample as it moves through the conduit by moving an integrated detector along the length of the separation conduit, wherein time and space dependent data obtained from successive scans of the analyte sample is stored, and wherein the data is used to represent successive scans of the analyte sample. Yet another aspect of the invention is directed to an apparatus for real time detection of elution of one or more analytes, including: a separation conduit, an admittance detector located immediately adjacent to the separation conduit, wherein one of the separation conduit and the admittance detector are configured to move relative to the other of the separation conduit and the admittance detector; and a driver configured to move the admittance detector back and forth along the length of the separation conduit wherein the admittance detector scans a length of the separation conduit and detects analyte as it moves through the length of the separation conduit.

In operation, the detector of the invention is moved repeatedly with high resolution back and forth along the separation conduit. Generally, an initial scan is performed, prior to analyte injection, and stored so that it may be subtracted from all subsequent scans after analyte injection. The initial, or blank, scan may include time and space dependent data, which is stored and subtracted from all corresponding scans after analyte injection.

The methods and apparatuses of the present invention have other features and advantages which will be apparent from or are set forth in more detail in the accompanying drawings, which are incorporated herein, and the following Detailed Description, which together serve to explain certain principles of the present invention.

BRIEF DESCRIPTION OF THE DRAWINGS

FIG. 1A, FIG. 1B, FIG. 1C and FIG. 1D illustrate an exemplary integrated detection apparatus in accordance with the present invention, wherein the integrated detector is shown in successive locations along the length of a separation conduit.

FIG. 4A, FIG. 4B and FIG. 4C illustrate top, enlarged and side views of an exemplary integrated detector of the apparatus of FIG. 2.

DETAILED DESCRIPTION

Figure 1A:
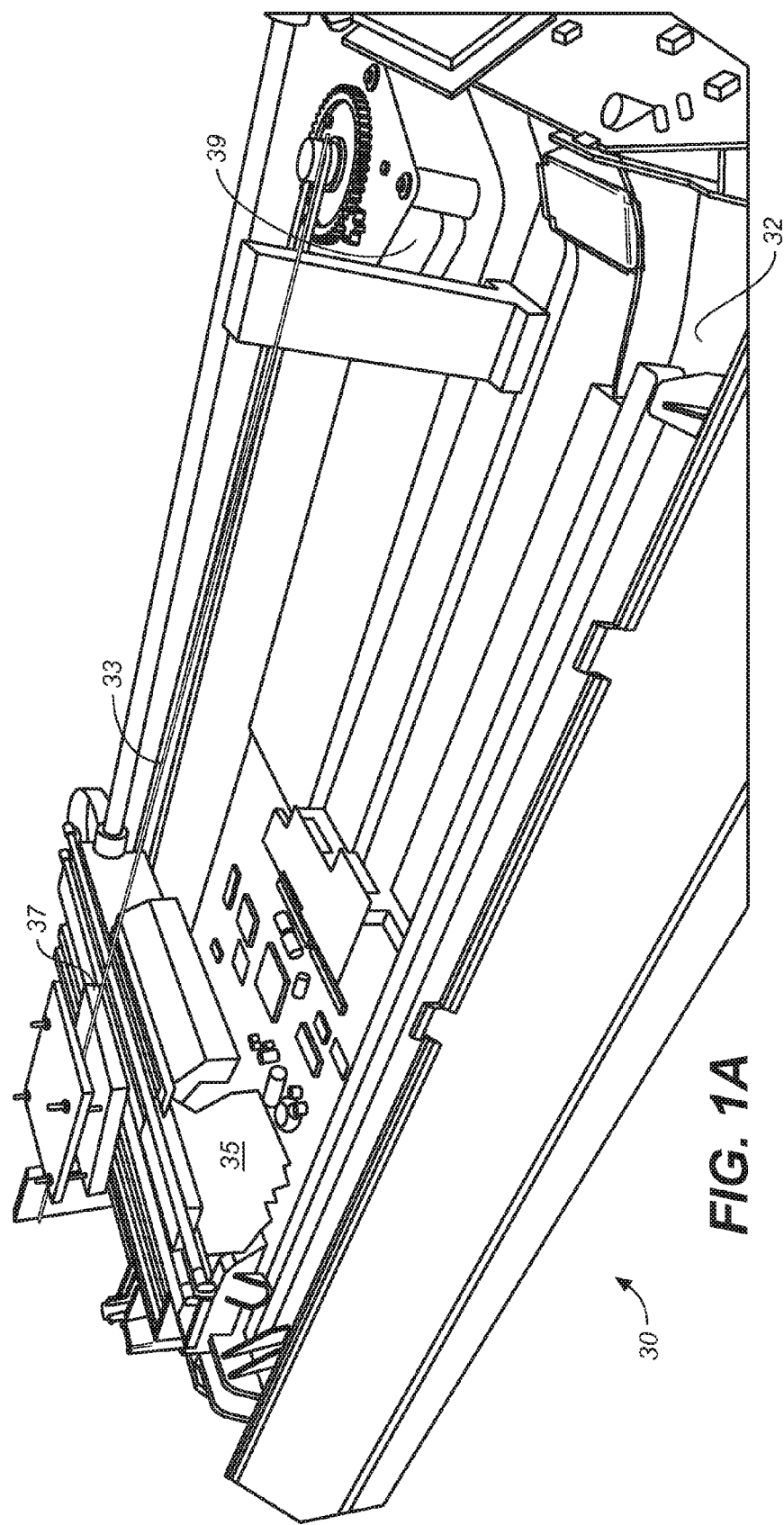

Reference will now be made in detail to various embodiments of the present invention(s), examples of which are illustrated in the accompanying drawings and described below. While the invention(s) will be described in conjunction with exemplary embodiments, it will be understood that present description is not intended to limit the invention(s) to those exemplary embodiments. On the contrary, the invention(s) is/are intended to cover not only the exemplary embodiments, but also various alternatives, modifications, equivalents and other embodiments, which may be included within the spirit and scope of the invention as defined by the appended claims.

The terms "a" and "an" are defined as one or more unless this disclosure explicitly requires otherwise. The term "substantially" is defined as largely but not necessarily wholly what is specified (and includes what is specified; e.g., substantially 90 degrees includes 90 degrees, and substantially parallel includes parallel), as understood by a person of ordinary skill in the art. In any disclosed embodiment, the terms "substantially," "approximately," and "about" may be substituted with "within [a percentage] of" what is specified, where the percentage includes 0.1, 1, 5, and 10 percent.

Further, a device or system that is configured in a certain way is configured in at least that way, but it can also be configured in other ways than those specifically described.

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, an apparatus that "comprises," "has," "includes" or "contains" one or more elements possesses those one or more elements, but is not limited to possessing only those elements. Likewise, a method that "comprises," "has," "includes" or "contains" one or more steps possesses those one or more steps, but is not limited to possessing only those one or more steps.

The feature or features of one embodiment may be applied to other embodiments, even though not described or illustrated, unless expressly prohibited by this disclosure or the nature of the embodiments.

When the dry reproduction process was invented by Chester Carlson in 1938, he called it electrophotography. It was later renamed Xerography by the Haloid Corp. (later Xerox). The whole image was generated at once in Carlson's invention. This was also the technique used in early Xerox machines. Today we know that a scanning imager provides greater resolution and fidelity. The same principle is used in scanners and copying machines. Certain aspects of the present invention adopt this philosophy to devise a detection system for open and packed capillary chromatography systems. In accordance with various aspects of the present invention, a packed capillary may include separation packing doped with inorganic fluors. Radiation absorbing analytes may cut down on the light reaching the fluors, and absorbing analytes may show up as negative fluorescence signals.

Figure 1C:
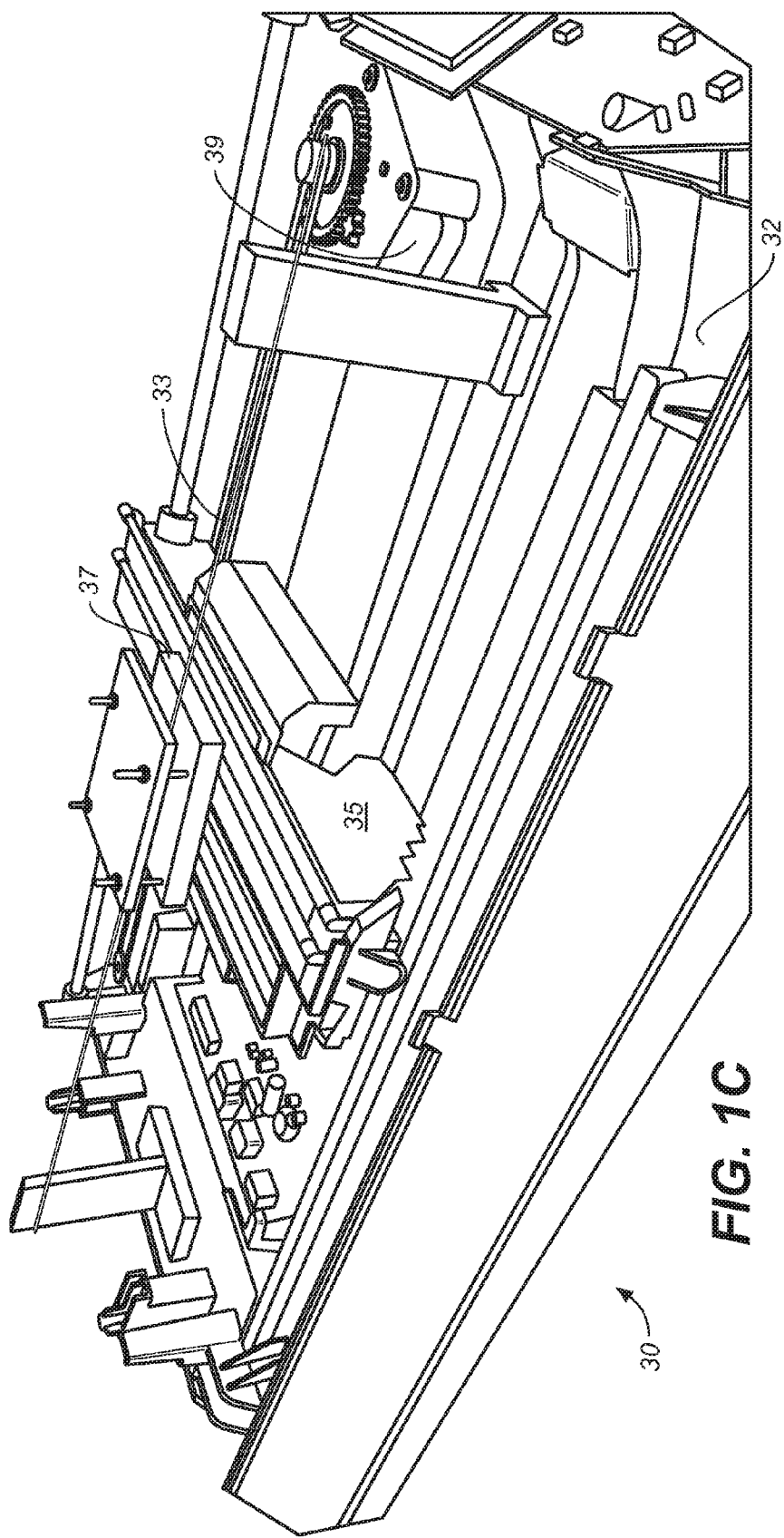
Figure 1D:
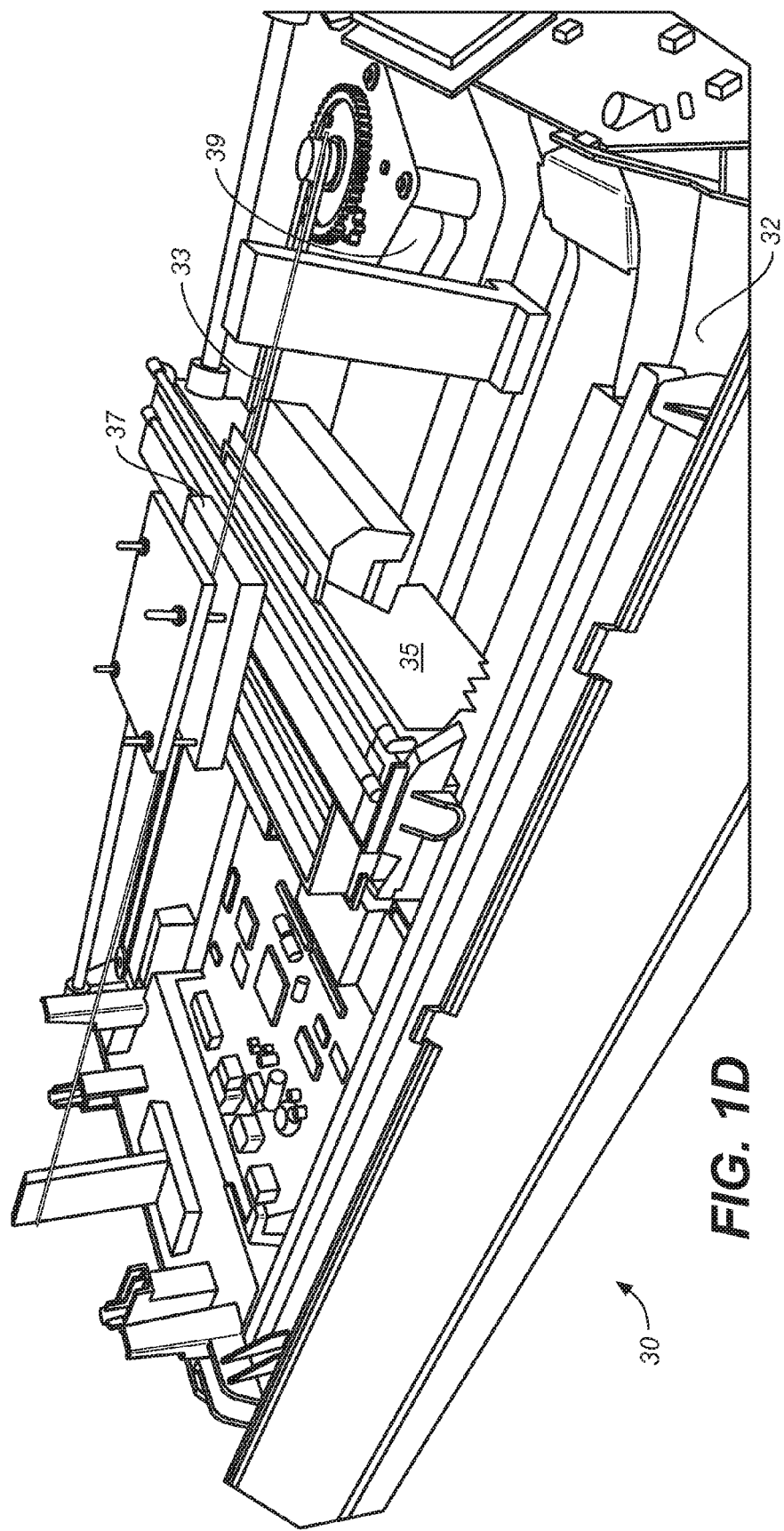

Turning now to the drawings, wherein like components are designated by like reference numerals throughout the various figures, attention is directed to FIG. 1, which illustrates an exemplary apparatus for scanning and detecting analytes in real time, and in which the apparatus is generally designated by numeral 30. The apparatus generally includes a stationary base 32, a separation conduit 33 (see FIG. 2A) mounted on the base, a carriage 35 movably supported on the base and configured to move along a length of the separation conduit, an integrated detector 37 mounted on the carriage and located immediately adjacent to the separation conduit, and a driver 39 moving the carriage relative to the base so that the integrated detector moves back and forth along the length of the separation conduit. The integrated detector is configured to scan the separation conduit and detect analyte as it moves through the separation conduit.

In various aspects, the base/carriage assembly of the present invention is similar to otherwise conventional flatbed scanner hardware that is configured for moving a scanning head back and forth relative to a flatbed. For example, relatively inexpensive existing flatbed scanner hardware currently provides 9600 dpi resolution, in which each dpi step is equivalent to 2.65 μm. Accordingly, the exemplary integrated detection apparatus 30 of the present invention utilizes to move carriage 35 and integrated detector 37 thereon back and forth along a length of separation conduit 33 in precise steps, as shown in FIG. 1A through FIG. 1D and FIG. 2A.

Figure 2A:
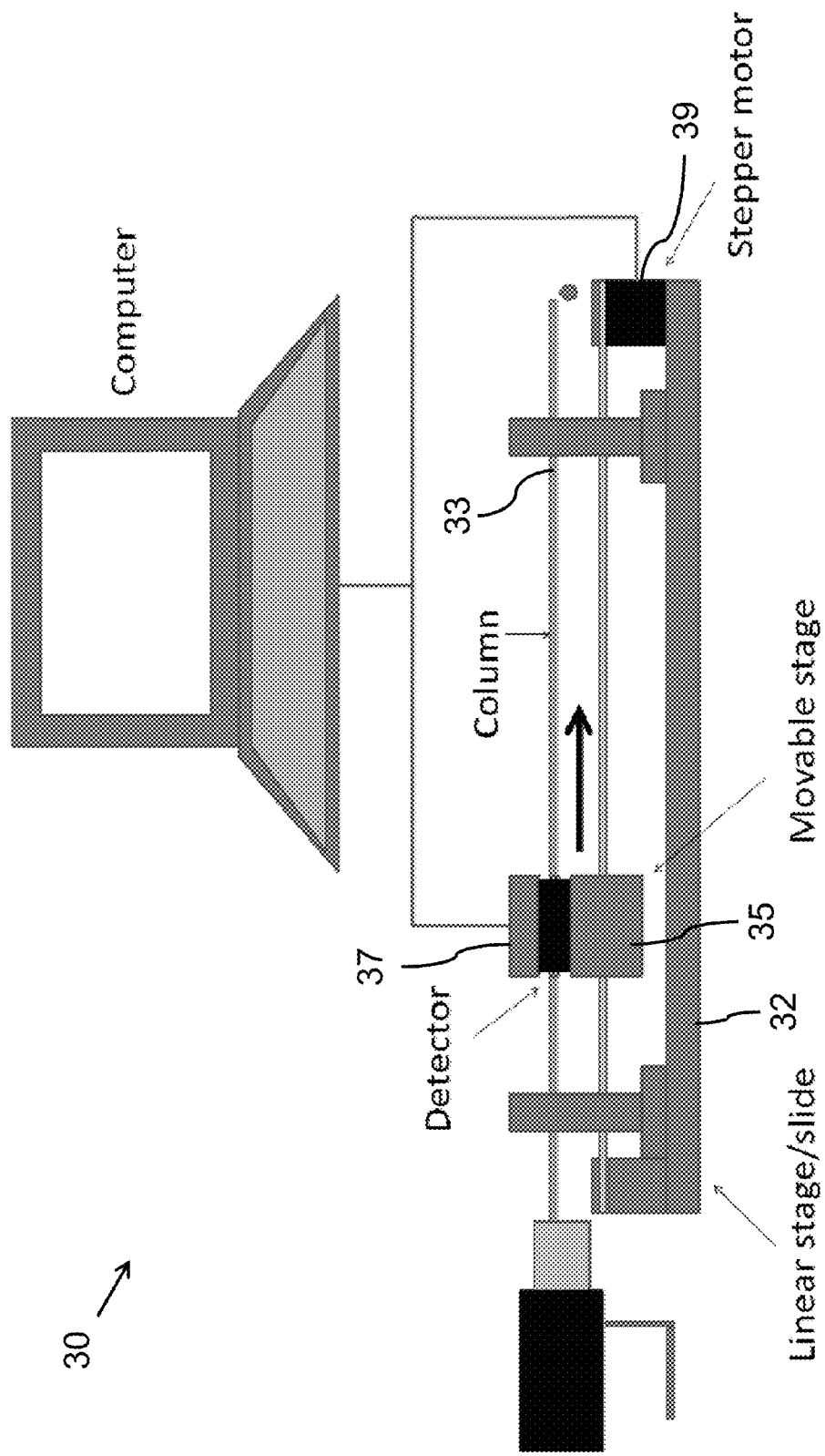
FIG. 2A and FIG. 2B are schematic side and top views of the apparatus of the invention of FIG. 1A.
Figure 2B:
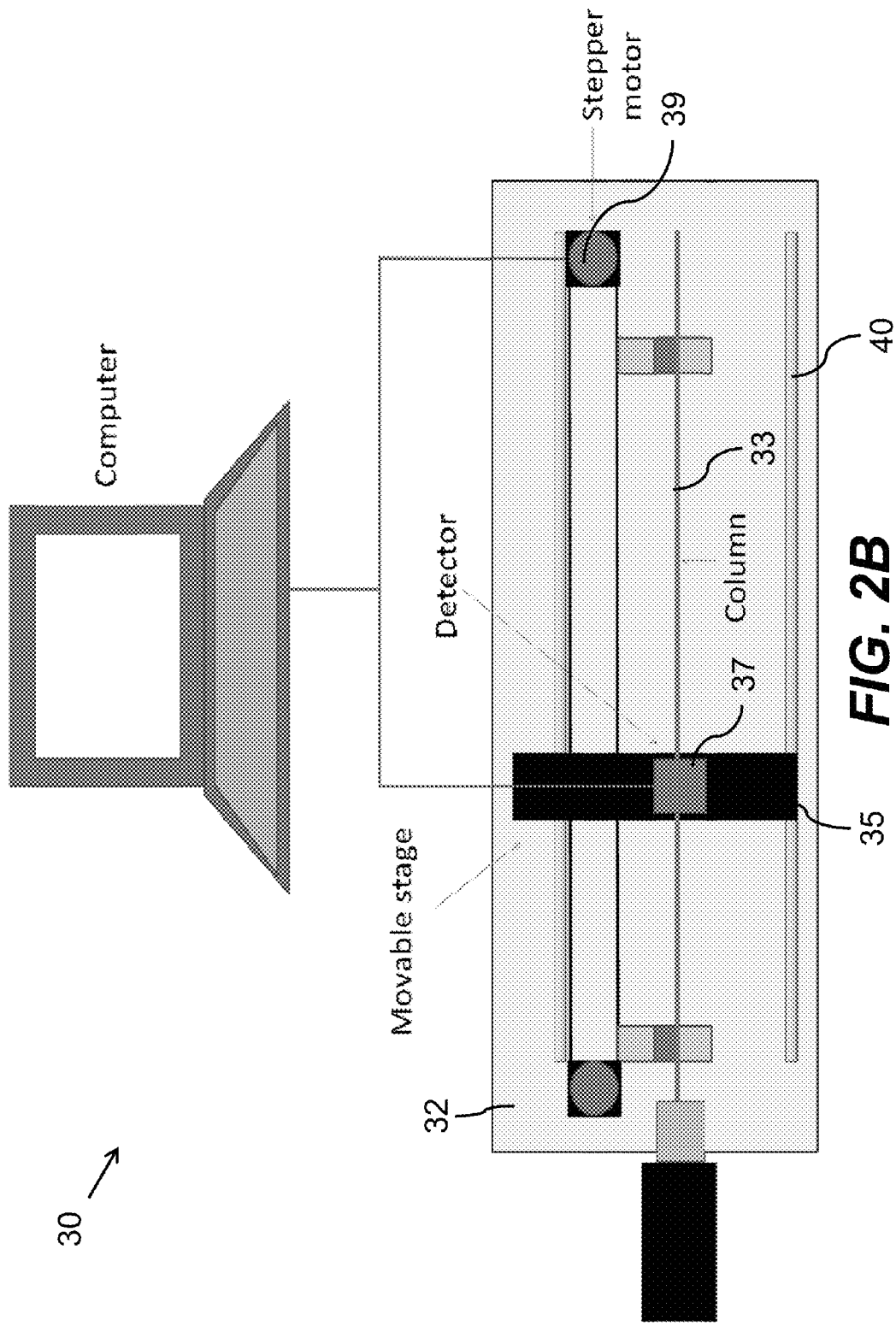

As shown in FIG. 2A and FIG. 2B, stationary base 32 includes a linear slide stage upon which carriage 35 may move in a linear direction. "Stationary base" is but a relative term in that stationary base 32 is an unmoving platform to which separation conduit 33 is mounted, and upon which the carriage moves upon and along a length of the separation conduit. One will appreciate that the stationary base (and apparatus 30 in general) may be a desk-top assembly or a standalone assembly.

The carriage or movable stage may be mounted to the stationary base by a linear slide 40 that extends substantially parallel to the separation conduit. The linear slide may be in the form of rails, rods, tracks, bearing assemblies or other suitable means to all the carriage to slide freely with respect to the base.

Integrated detector 37 is mounted on the carriage such that the detector moves along separation conduit 33. The integrated detector includes an excitation source and a corresponding sensor that are work together as a unit, moving together along the separation conduit. In various embodiments, the integrated detector may be a conductometric (conductance or admittance) detector including an excitation electrode and corresponding pickup electrode. In various embodiments, the integrated detector may be an optical detector (absorbance or fluorescence) including a light source and a corresponding sensor. And in various embodiments, the integrated detector may include a combination thereof. In the illustrated embodiment, the separation conduit is a capillary column, which one will appreciate may be suitable for chromatography, capillary electrophoresis, and other analysis of samples and materials located within a separation conduit.

Figure 3:
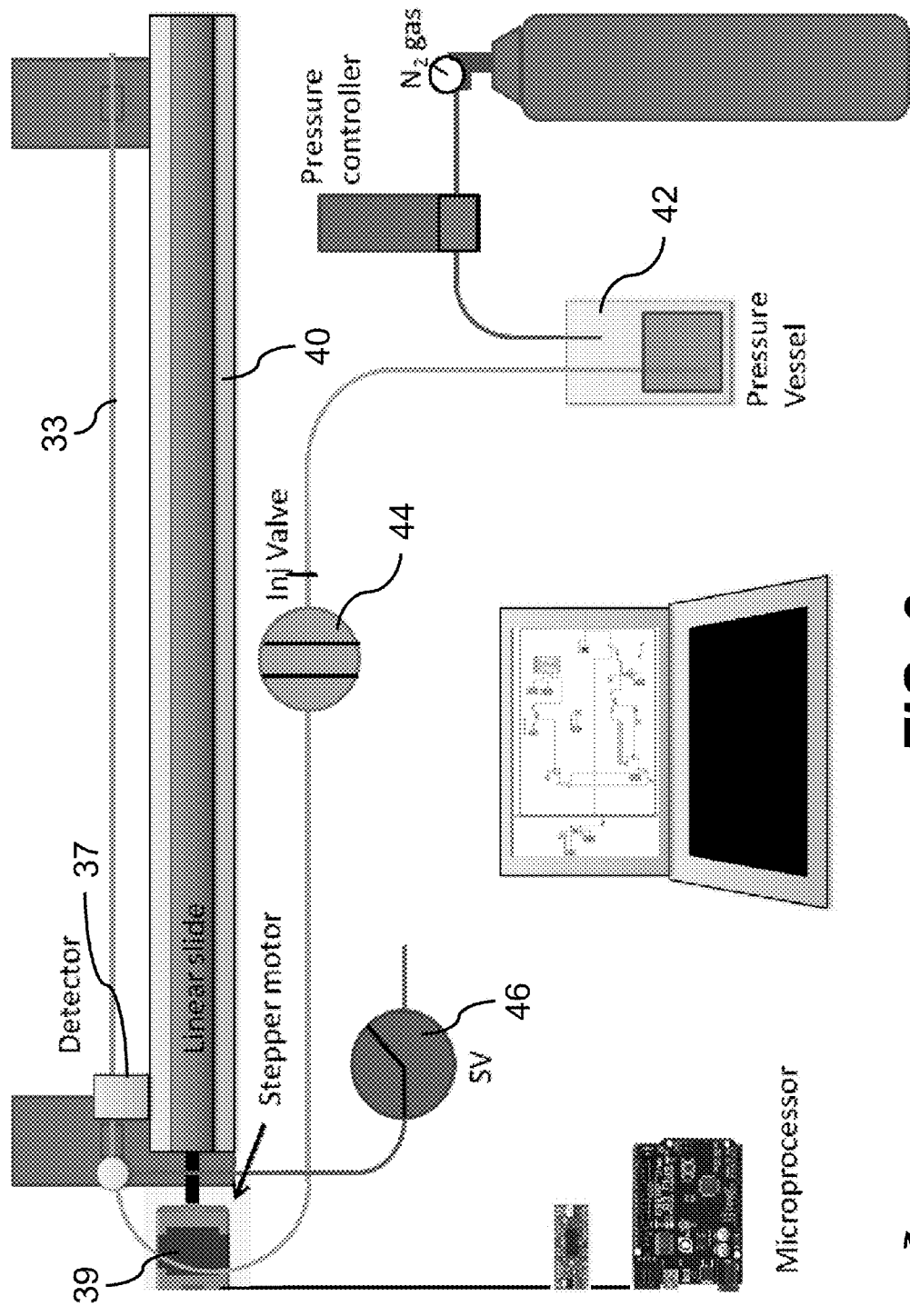
FIG. 3 is a schematic view of other aspects of the apparatus of FIG. 1.

With reference to FIG. 3, the apparatus includes a pressure source 42 for pumping eluent through an injection valve 44 into and through separation conduit 33, and a sample valve 46 to introduce a sample into the eluent that travels through the separation conduit. In the illustrated embodiment, the pressure source is a pressure vessel that is pressurized by compressed gas, however, one will appreciate that other suitable means may be used including, but not limited to, syringes and/or other forms of mechanical pumps.

Driver 39 is configured to precisely move the carriage along the linear slide relative to the base as well as the separation conduit. The driver may be in the form of a stepper motor which allows the carriage to move in precise increments, for example, the above mentioned 2.65 μm. One will appreciate that the stepper motor may be configured to move the carriage in other increments depending upon desired fidelity as well as the configuration of the motor and other components.

The driver, in turn, is operated by a suitable controller 47. A computer and/or other suitable microprocessor may be configured to actuate the driver to precisely control movement of the carriage and detector along the length of the separation conduit. In accordance with the present invention, the driver may move the carriage and detector forward and/or backward along the entire detectable length of the separation conduit so as to sweep and scan the entire detectable length, or the driver may be configured to move the carriage intermittently back and forth along that portions of the detectable length of the separation conduit. For example, if the conduit length is 0-100 units, an exemplary scan sequence may be 0-10, 0-12, 1-14, 1-16, 2-18, etc., until the detectable length of the conduit has been scanned. One will appreciate that the driver may be controlled to scan the carriage and detector along successive portions, overlapping portions, or combinations thereof in order to concentrate on particular portions of interest along the detectable length of the conduit. One will also appreciate that the driver may be controlled to perform multiple scans of the detectable length (or portions thereof) of the conduit.

With reference to FIG. 4A, FIG. 4B and FIG. 4C, separation conduit 33 passes through integrated detector 37. The detector may be equipped with two snugly fitting stainless steel tubular electrodes separated by a central ground plane metal foil with insulating tape on either side. In the illustrated embodiment, the effective electrode separation is about 300 µm, however, one will appreciate that other materials and separation distances may vary depending upon the desired configuration.

The tubular electrodes include an excitation electrode 49 and a pickup electrode 51 which are separated by the central ground plane, that is, grounded planar electrode or shield 53. One will appreciate that the specific size and shape of the electrodes may vary, for example, the excitation and pickup electrodes may have a U-shape or other suitable shape.

Figure 7:
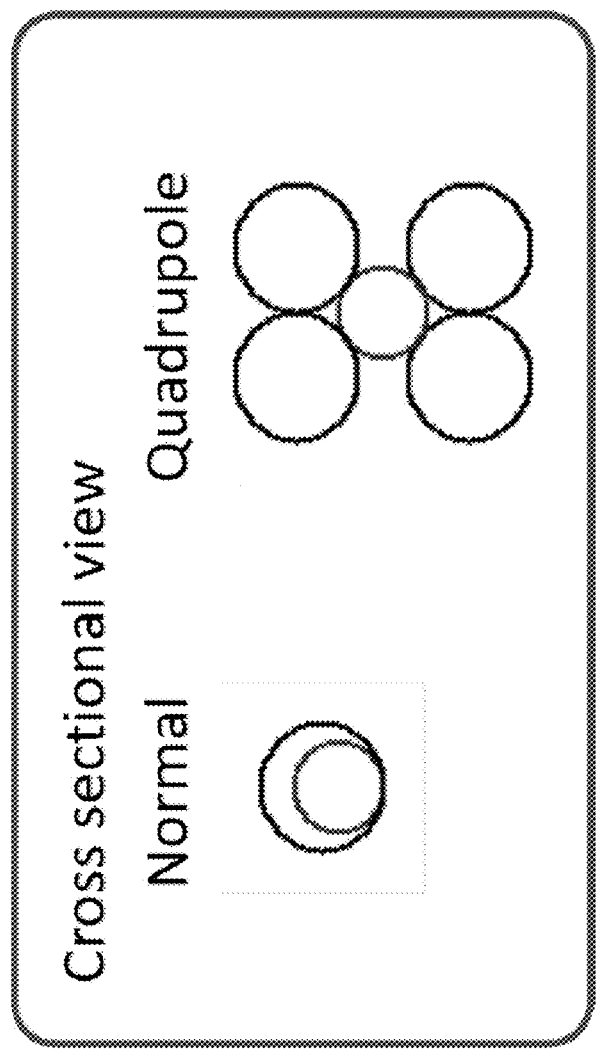
FIG. 7 illustrates an exemplary quadrupole structure that may be incorporated into an integrated detector in accordance with the present invention.

In various embodiments, a quadrupole electrode configuration may be utilized, as shown in FIG. 7. Four electrodes are utilized including one pair for excitation, one pair for pickup. Such a configuration has been shown to provide four times better signal to noise ratio.

In operation, the excitation electrode excites liquid containing analyte(s) inside the separation conduit through the walls of the separation conduit, and that excitation is traveling to the other side of the shield and is operably coupled to the pickup electrode through the wall of the separation conduit. Thus, the mobility of ions or conductively of the analyte-containing liquid may be detected using the excitation/pickup electrode combination.

With an exemplary structure of the integrated detector described, the operation of the detector may now be discussed.

Electrical conductivity is the hallmark property of an ion in solution and many ions such as sulfate perchlorate, methanesulfonate, sodium, potassium, etc. have no useful optical absorption. Even the ubiquitous chloride absorbs very weakly and that at a wavelength where solvent absorption becomes significant. In addition, most such ions cannot be chemically converted/derivatized to optically detectable forms. In other words, optical detection is not an option for a variety of analytes.

In terms of imaging, which requires that the interior of an open or packed column can be probed from the outside, it has long been known that an alternating exciting voltage can penetrate most dielectric materials (polymer, glass, etc.). Originally this technique was called Oscillometry (see e.g., Oscillometry and Conductometry, Erno Pungor, Pergamon, 1965) with relatively high frequencies (several hundred kHz to several MHz) being used with glass containers. Presently the technique is more commonly called Capacitively Coupled Contactless Conductivity Detection (C4D). The term is somewhat misleading in that the electrodes may not be in contact with the fluid but they are in contact with the walls containing the fluid. In addition such detectors do not truly measure the conductance of the solution but its admittance (reciprocal of impedance), a frequency dependent quantity. For a given system, only within a limited frequency and conductance range will the admittance signal be related to the actual conductivity. Nevertheless, to conform to present use, we refer to such detectors hereinafter as C4D although they will be more correctly called admittance detectors. In its simplest, and by far the more common form introduced in 1998, it is used with glass or silica capillaries, with ring shaped electrodes, typically ~1 mm apart. See Reference (17) below. The alternating probe voltage is applied on one electrode (both high and low frequencies have been used), it travels through the tube wall, is attenuated by the solution resistance and then travels through the wall again to be picked up by the second electrode and is then amplified and rectified. The output voltage is thus related reciprocally to the resistance of the solution between the electrodes. C4D and its applications have been repeatedly reviewed by Kuban and Hauser, most recently in 2013. See Reference (18) below.

Although imaging of CE or HPLC separations have not been done by C4D, some work by the group of Paull is worthy of discussion. In 2008, they described the fact that by manually moving such a detector along the length of a packed capillary column and stopping and noting the detector output, it is possible to assess how uniformly the column is packed. See Reference (19) below. In our experience virtually no column (in fact regardless of how well it is packed) produces exactly the same detector output at all positions on the column. These variations are substantial and are only accentuated greatly in the presence of packing inhomogeneity. Just by looking at the detector output therefore it becomes possible to detect the presence of an analyte only at relatively high analyte concentrations. Within these limitations, again by manually moving the detector to different locations on the column (with a resolution anywhere between 1 and 15 mm), stopping and taking readings they were able to assess how (separately) injected nitrite and nitrate peaks broadened as they moved down the column. See References (19) and (20) below. In a more recent paper they made monolithic columns from different monomers and showed (again by manually moving a detector along the column) that different signals are obtained when different monomers are used. See Reference (22) below.

Very high resolution capacitance-to-voltage (C2V) digital converters that measure the capacitance between two probe electrodes have been inexpensively available for some time.

In accordance with various aspects of the present invention, electrodes similar to the electrodes that are used for C4D may be connected to the inexpensive C2V device and this de facto behaves as a conductivity detector. See, e.g., Reference (23) below.

Figure 5A:
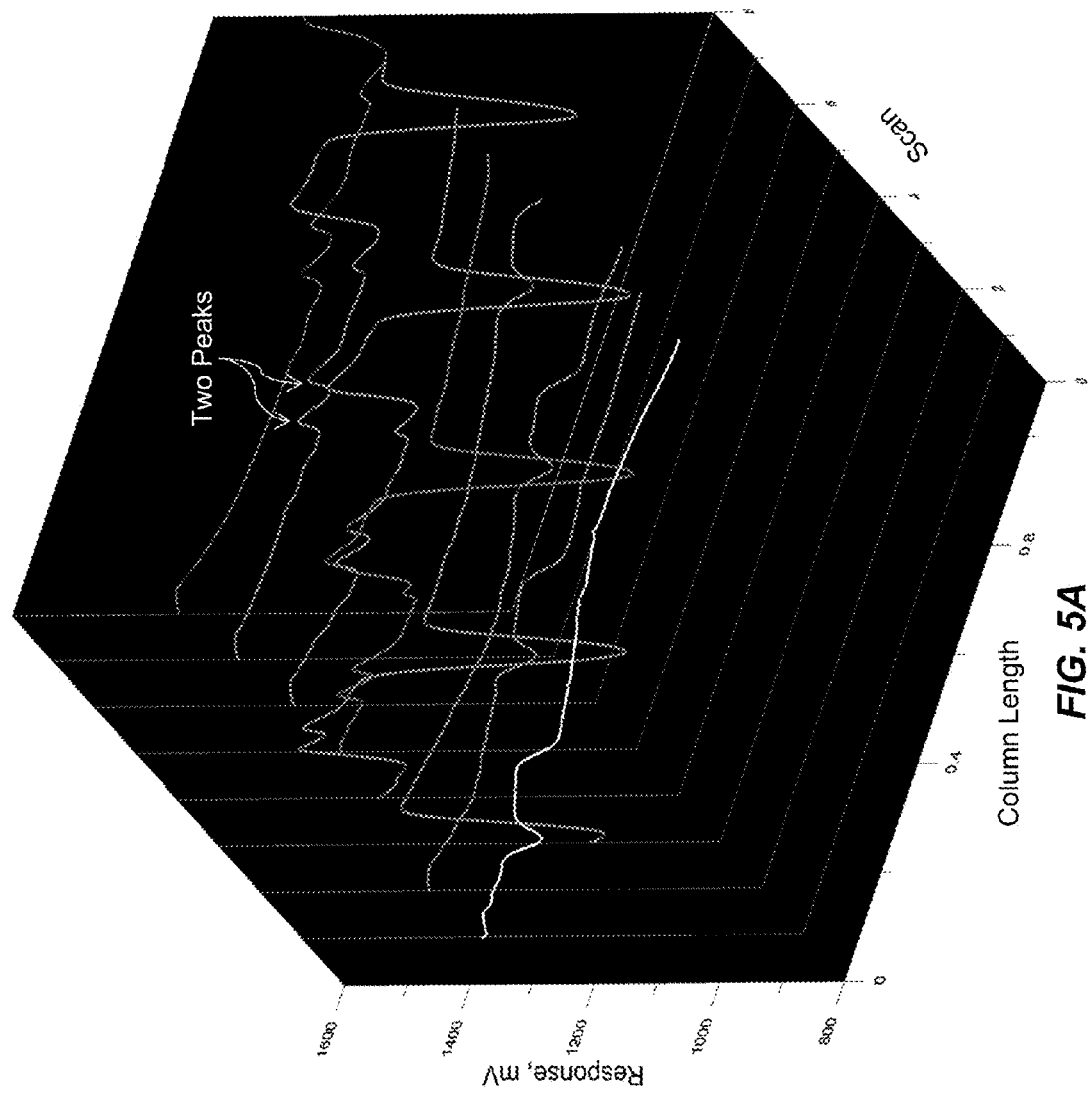
FIG. 5A and FIG. 5B illustrate scans of the integrated detector along the separation conduit, scanning away from and toward a sample injector, respectively.
Figure 5B:
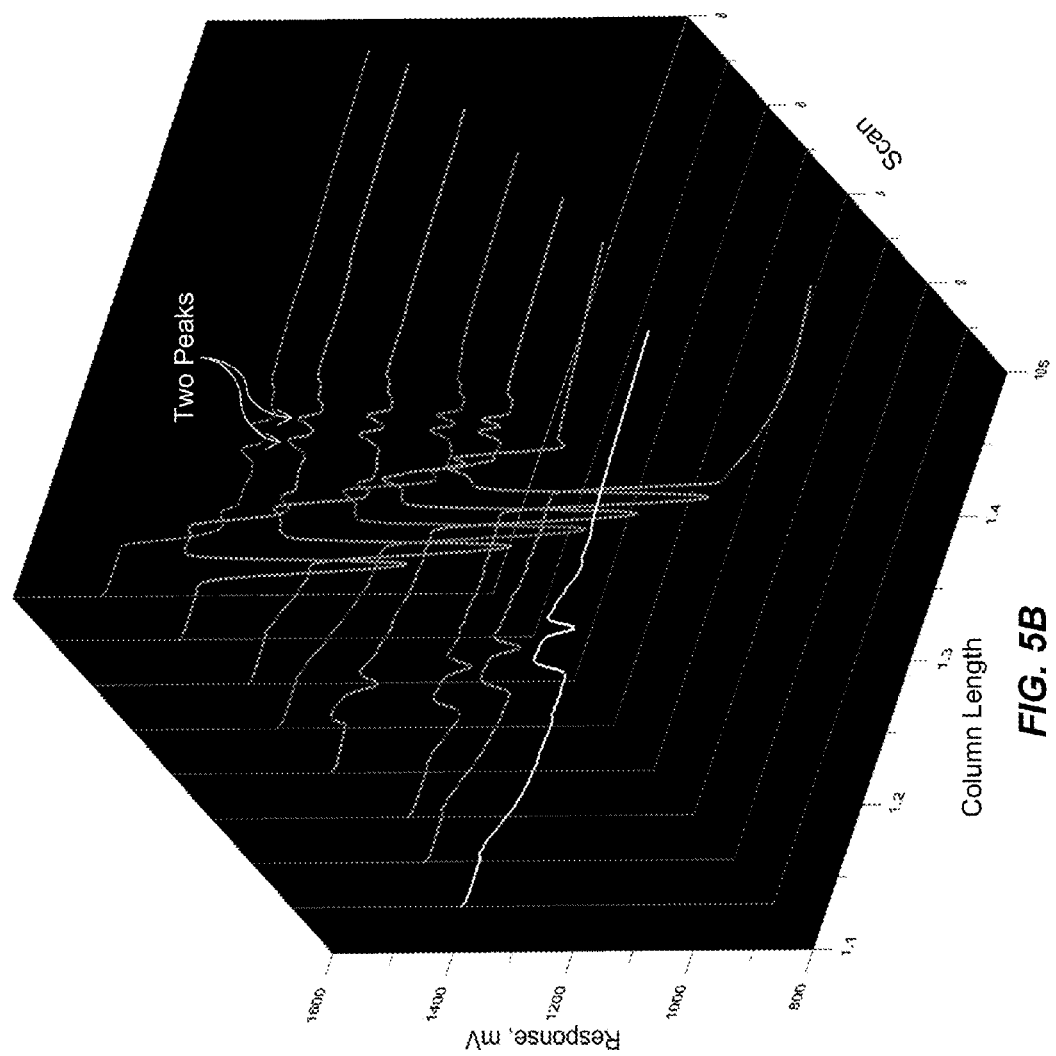

Turning now to FIG. 5A and FIG. 5B, each scan along the detectable length of the separation conduit may be processed and analyzed to provide a graphical representation of the analyte(s) passing through separation conduit. FIG. 5A and FIG. 5B are three-dimensional graphs showing the detected scanned responses of a sample passing through the separation column along the detectable length of the separation conduit for eight successive scans. The horizontal X-axis represents the position of the detector along the detectable length of the separation conduit or column, the vertical Y-axis represents the measured response in mV detected by the integrated detector at any given position along the detectable length, and the perpendicular Z-axis represents number of each successive scan along the detectable length.

For example, and with reference to FIG. 5A, scan 3 has a significant downward dip at the injection end of the conduit (i.e., column length 0) that shows the beginning of the water pressure shock preceding the introduction on analytes into the conduit. Scans 4, 5, 6 and 7 show the progression of the downward dip as the water pressure shock moves or flows down the detectable length of the conduit.

Similarly, and with continued reference to FIG. 5A, scan 5 shows the beginnings of two upward peaks that represent two analytes. Since the analytes enter the conduit after the water pressure shock, the two peaks appear to the left of the downward dip. Scans 6, 7 and 8 show the peaks becoming better defined as the two analytes separate while moving down the length of the separation conduit. As such, FIG. 5A illustrates the process of separation develop as corresponding analytes move through the separation conduit.

In contrast, FIG. 5B illustrates the successive "return" scans. The significant downward dip is again identifiable in return scans 3-7, and the upward peaks are again identifiable in scans 5-8. As these scans are "return" scans in which the detector moves backwards towards the injection end of the conduit, the downward peaks are now to the left of the upward peaks. This reversal is due to the detector first detecting the water shock preceding the analytes as the detector is moves and scans in reverse.

Figure 6A:
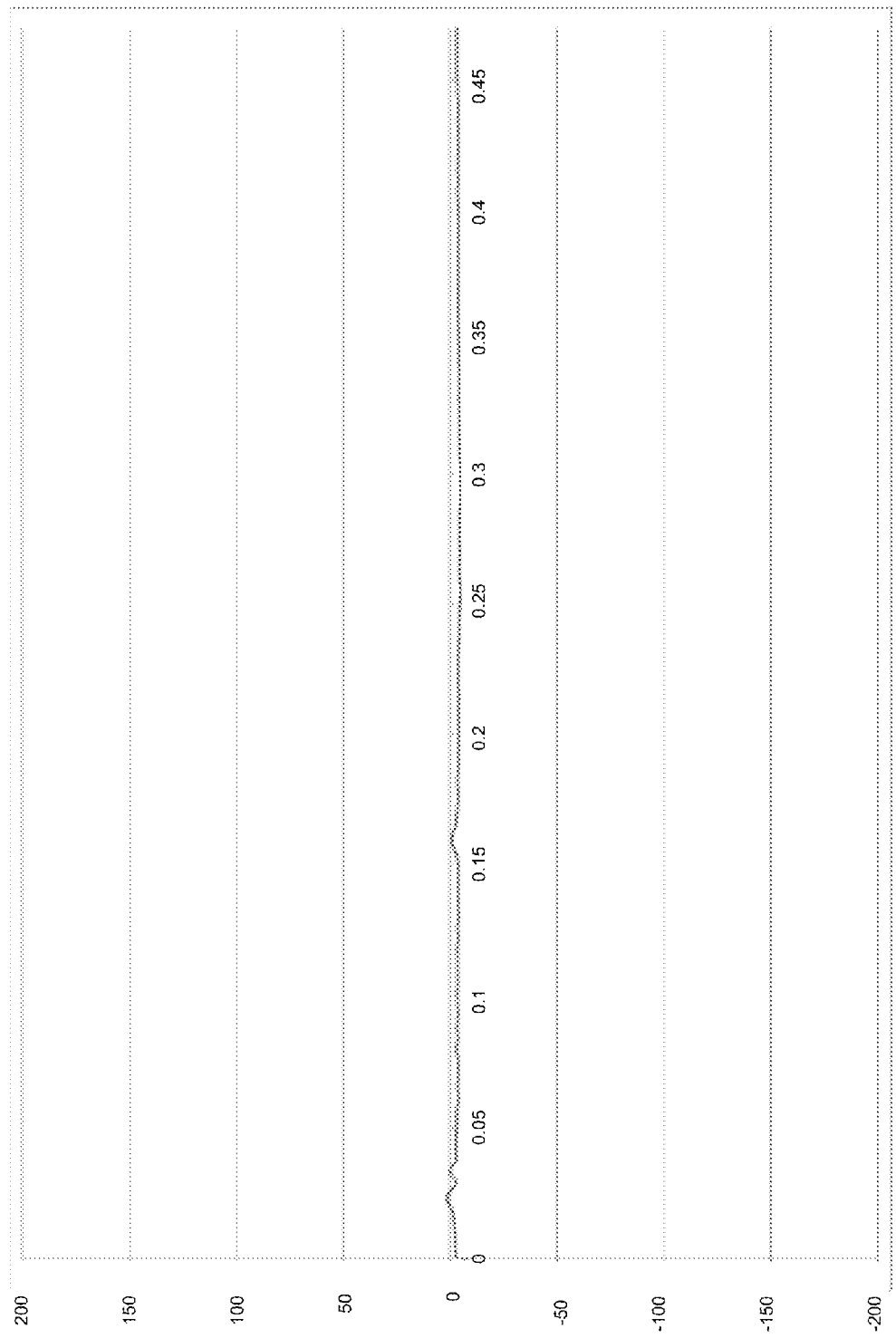
FIG. 6A, FIG. 6B, FIG. 6C, FIG. 6D, FIG. 6E, FIG. 6F, FIG. 6G, FIG. 6H, FIG. 6I, FIG. 6J, FIG. 6K and FIG. 6L illustrate gradual development of separation scanned by the integrated detector of the apparatus of FIG. 2.
Figure 6B:
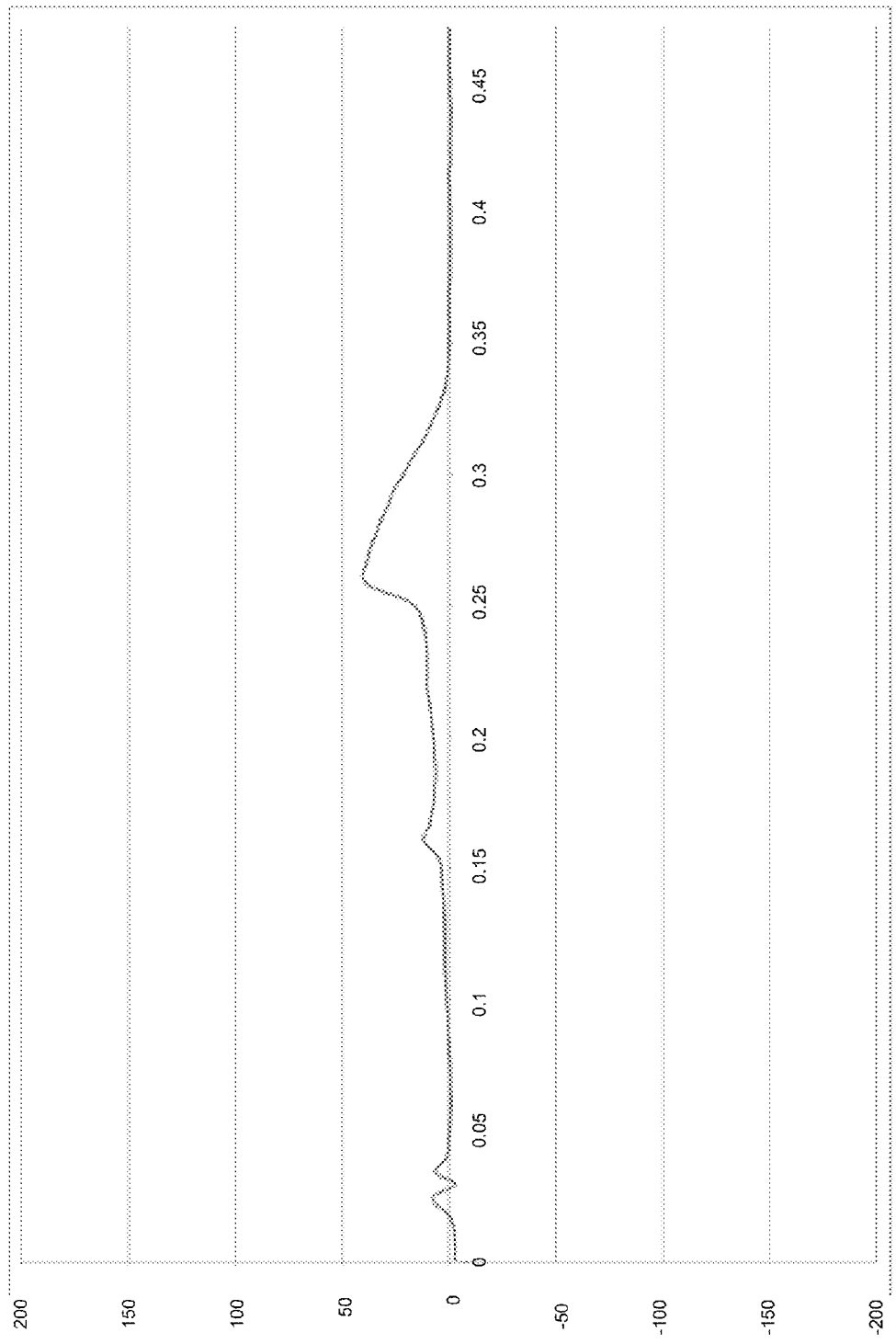
Figure 6C:
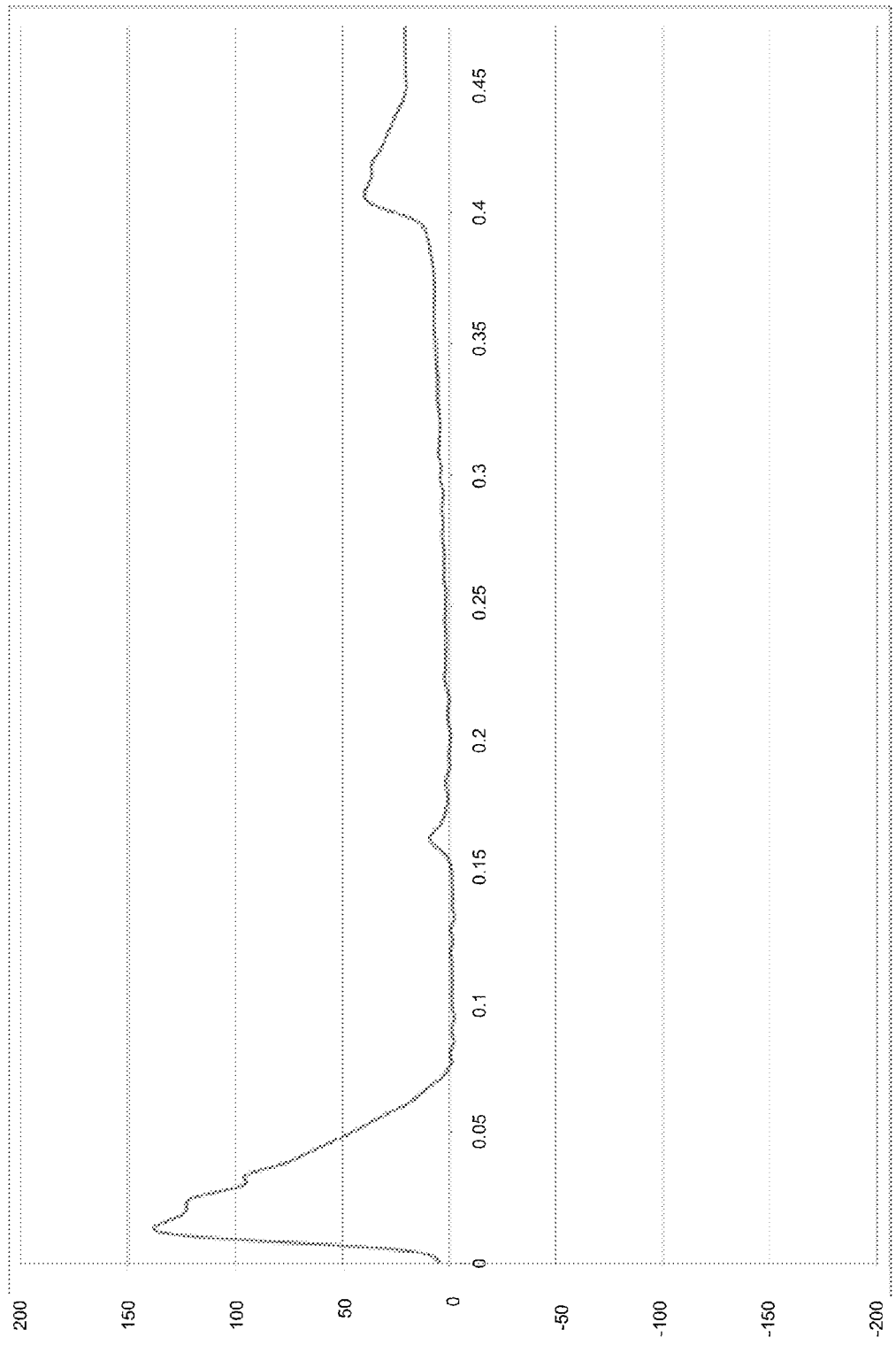
Figure 6D:
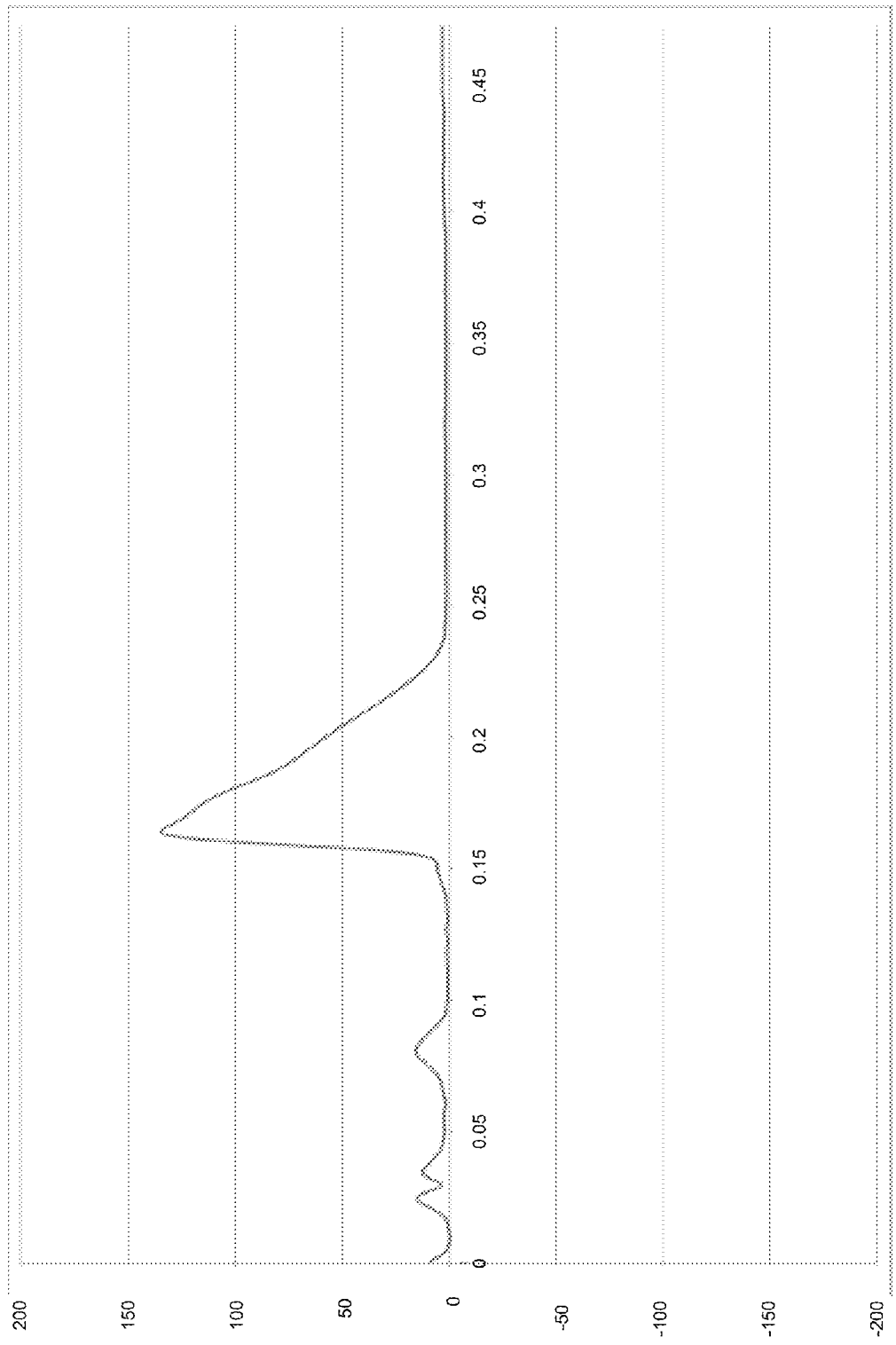
Figure 6E:
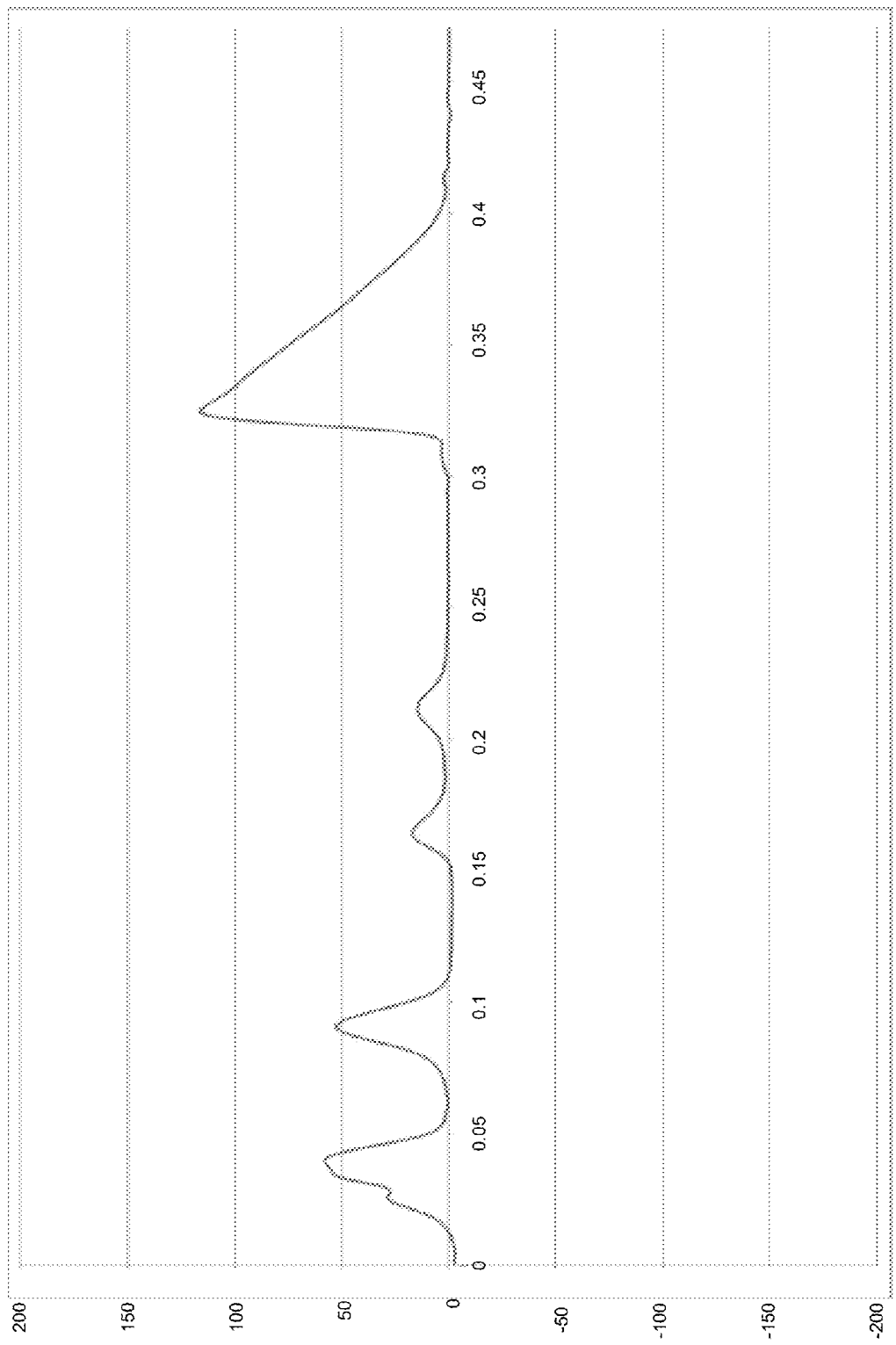
Figure 6F:
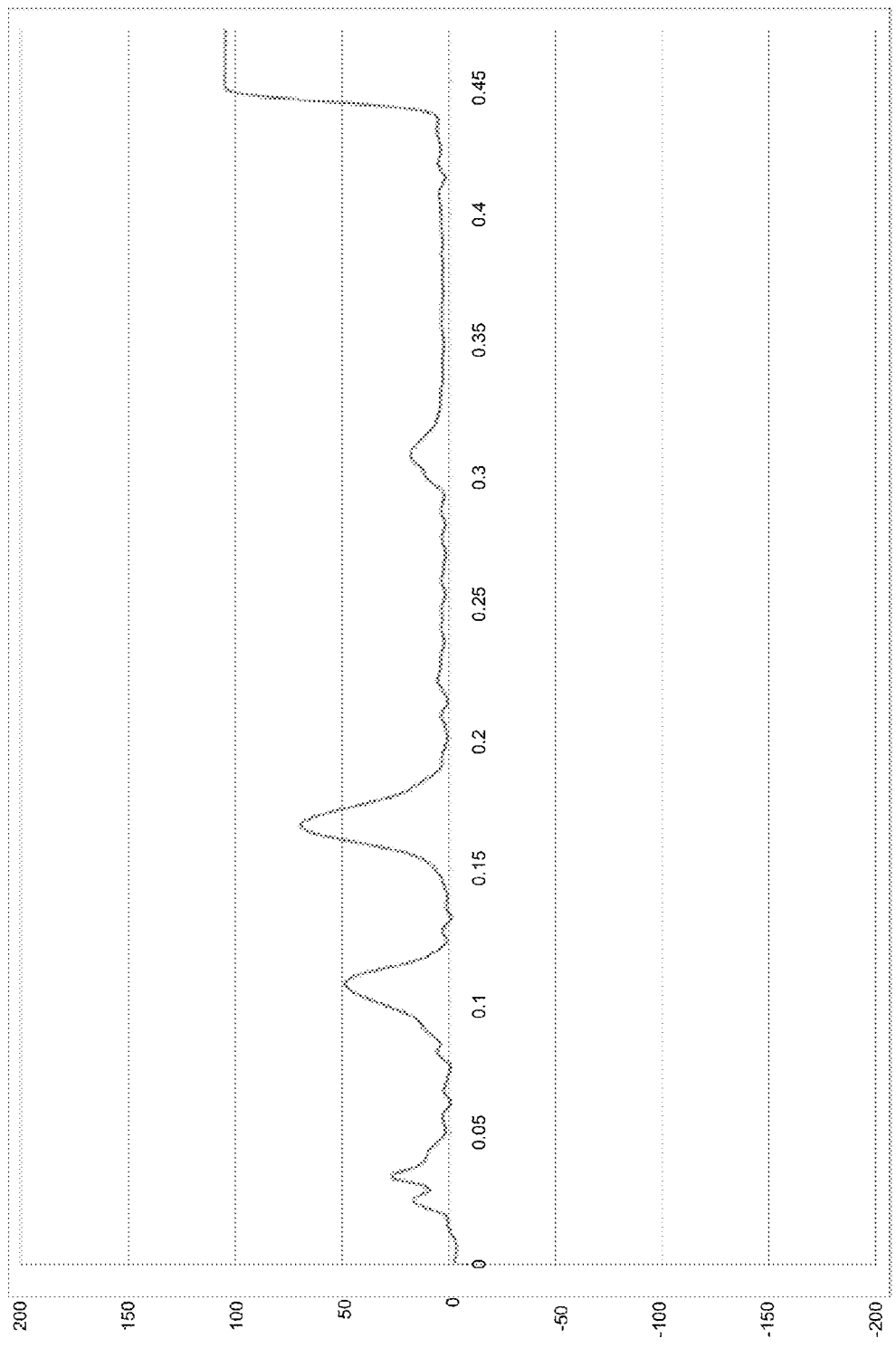
Figure 6G:
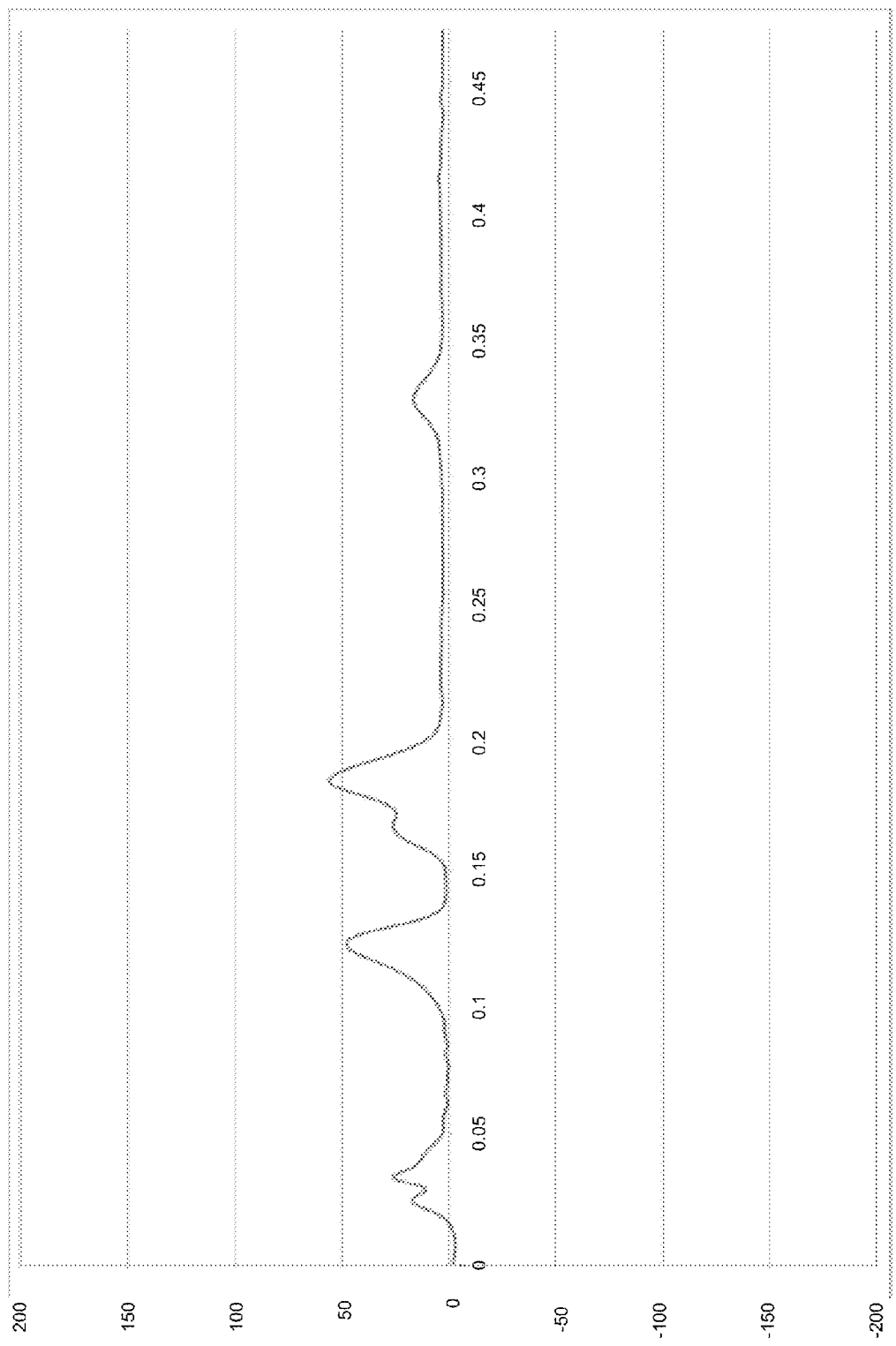
Figure 6H:
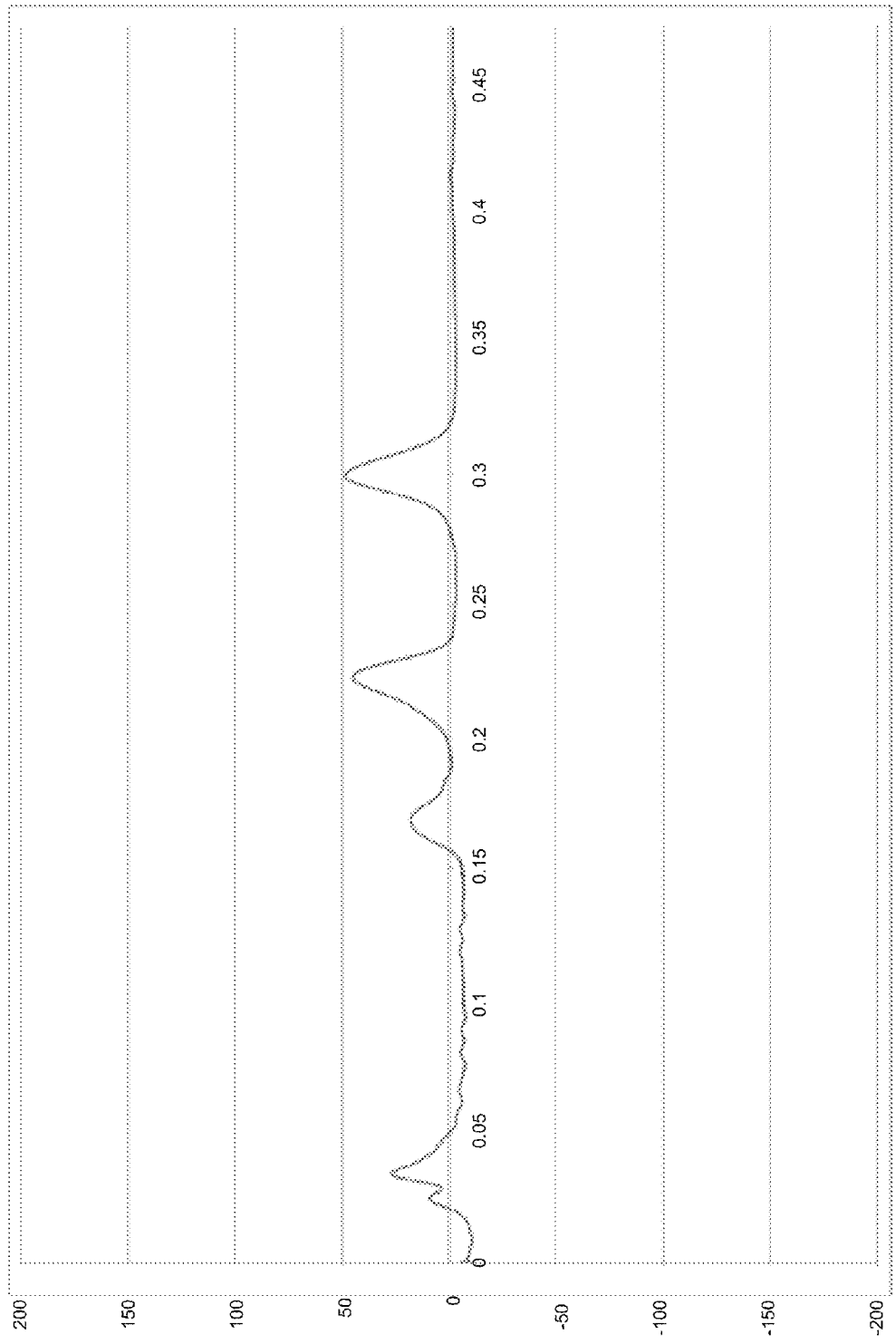
Figure 6I:
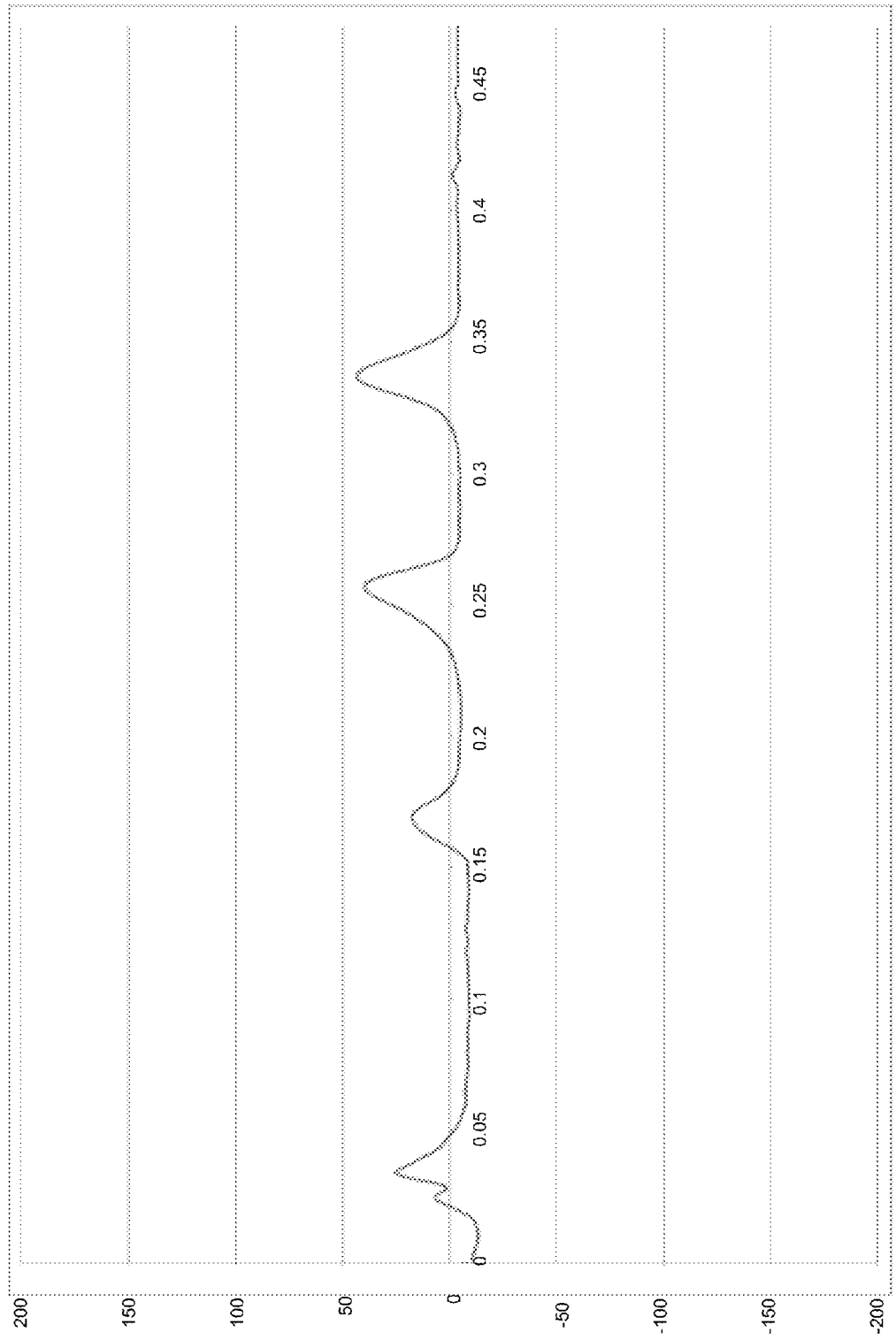
Figure 6J:
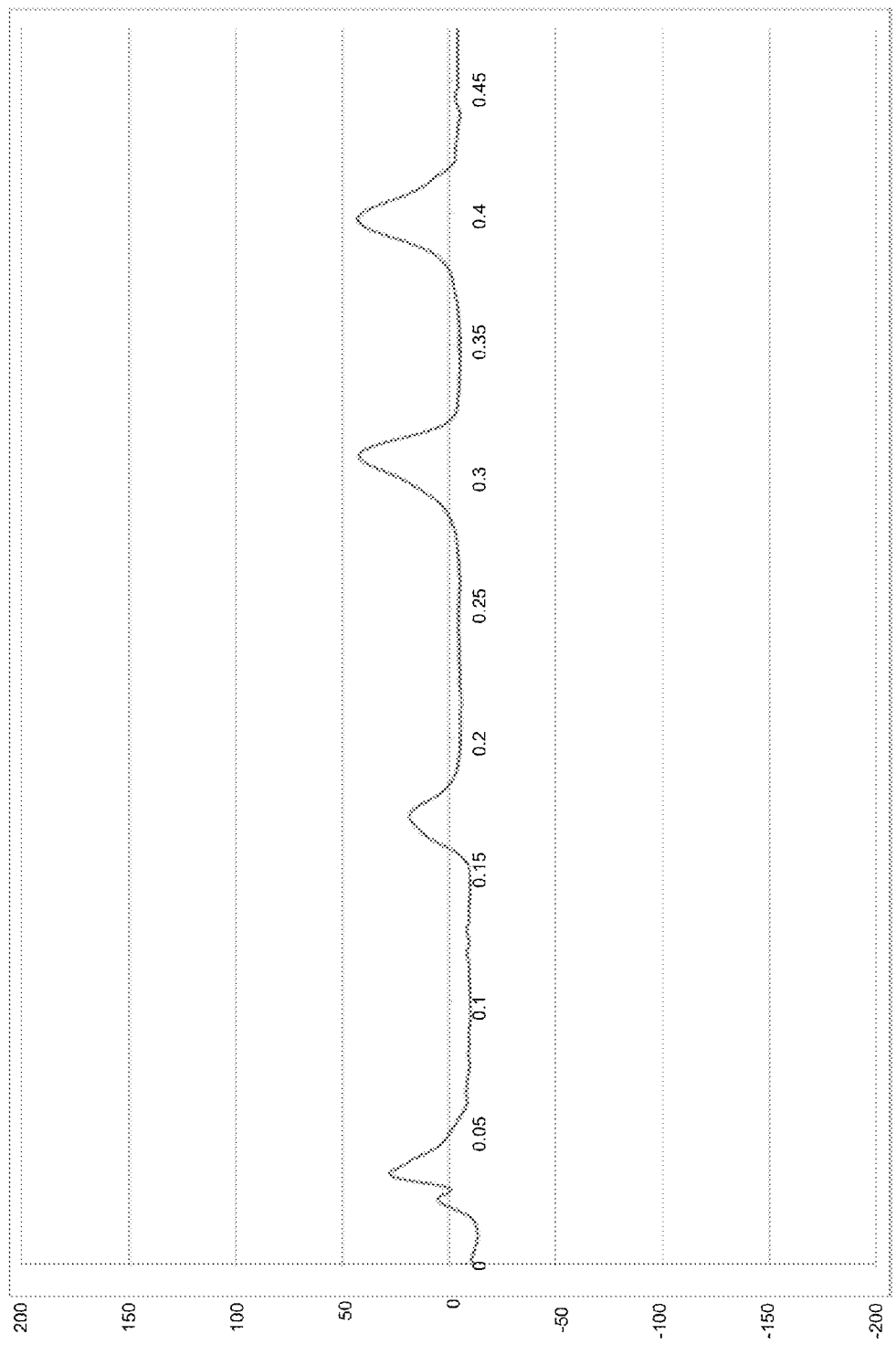
Figure 6K:
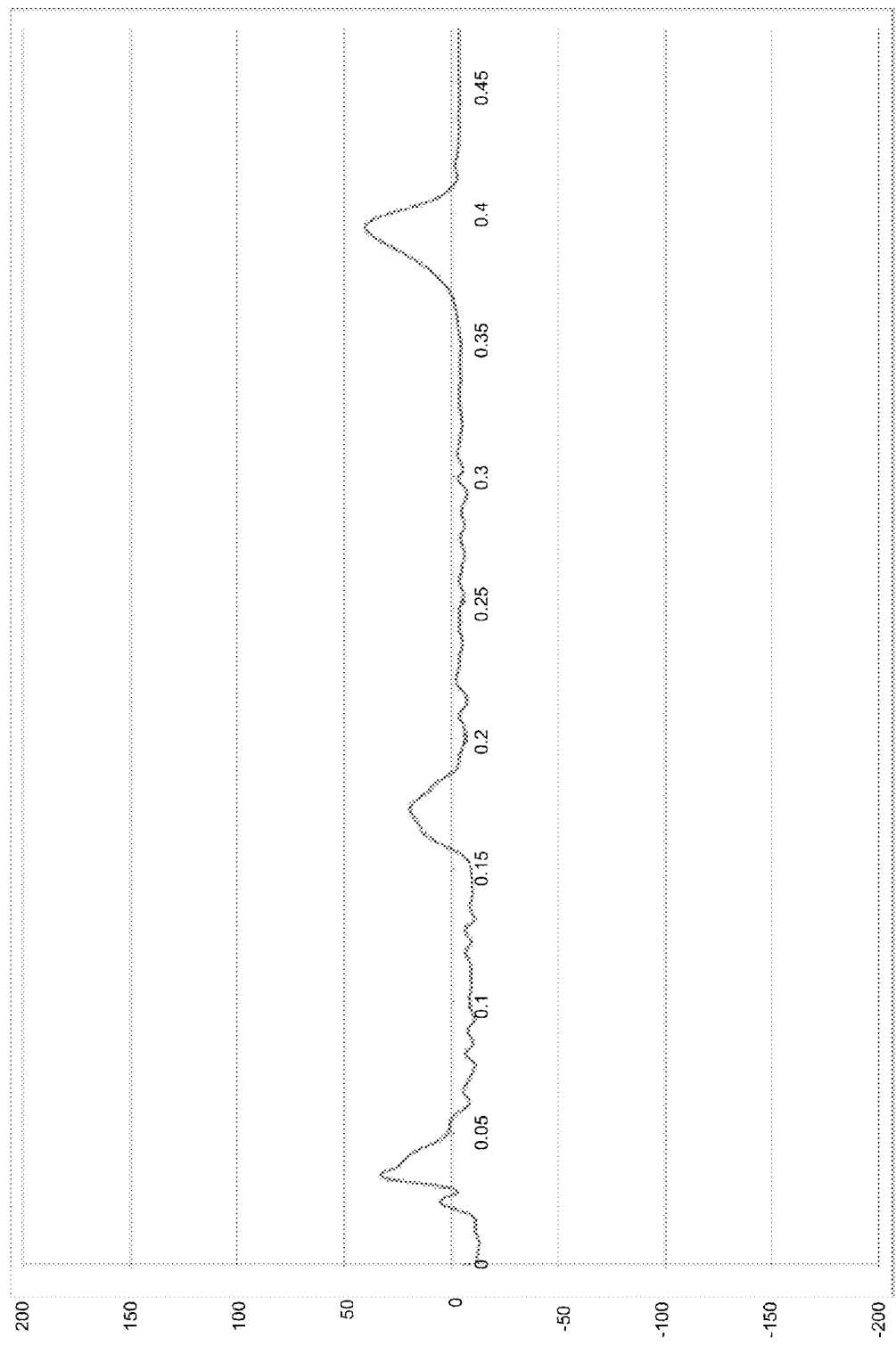
Figure 6L:
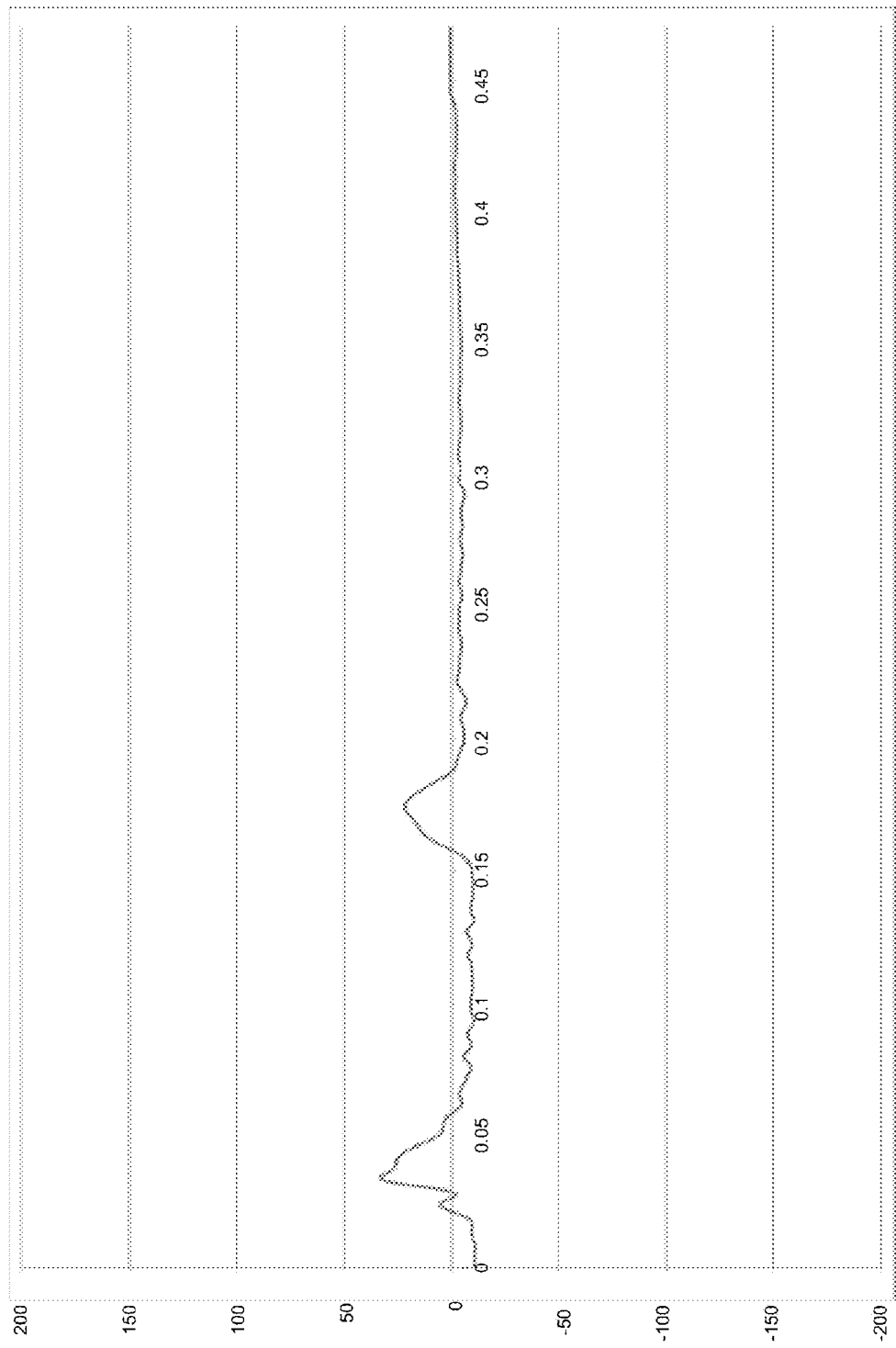

FIG. 6A through FIG. 6L illustrates successive scans along the detectable length of the conduit, but unlike FIG. 5A discussed above, these figures simply show individual plot lines representing each successive scan. For example, a significant peak is captured in the third scan (FIG. 6C), shown to progress down the conduit in the fourth scan (FIG. 6D), and clearly identifiable at the end of conduit in the fifth scan (FIG. 6E). Similarly, other peaks representing various analytes are shown to progressively move left-to-right as the respective analytes move through the conduit.

In other embodiments, carriage 35 may be configured to support integrated optical detector, in addition to or instead of the above integrated conductometric detector described above. For example, optical detectors of the type illustrated in FIG. 8A and FIG. 8B may be mounted on the carriage to scan the separation conduit alone or in parallel with a conductometric detector. Alternatively, such optical detectors may be incorporated into the same detector body as the above described integrated detector. Providing such optical detectors may increase the capabilities of the detection apparatus of the present invention.

Figure 8A:
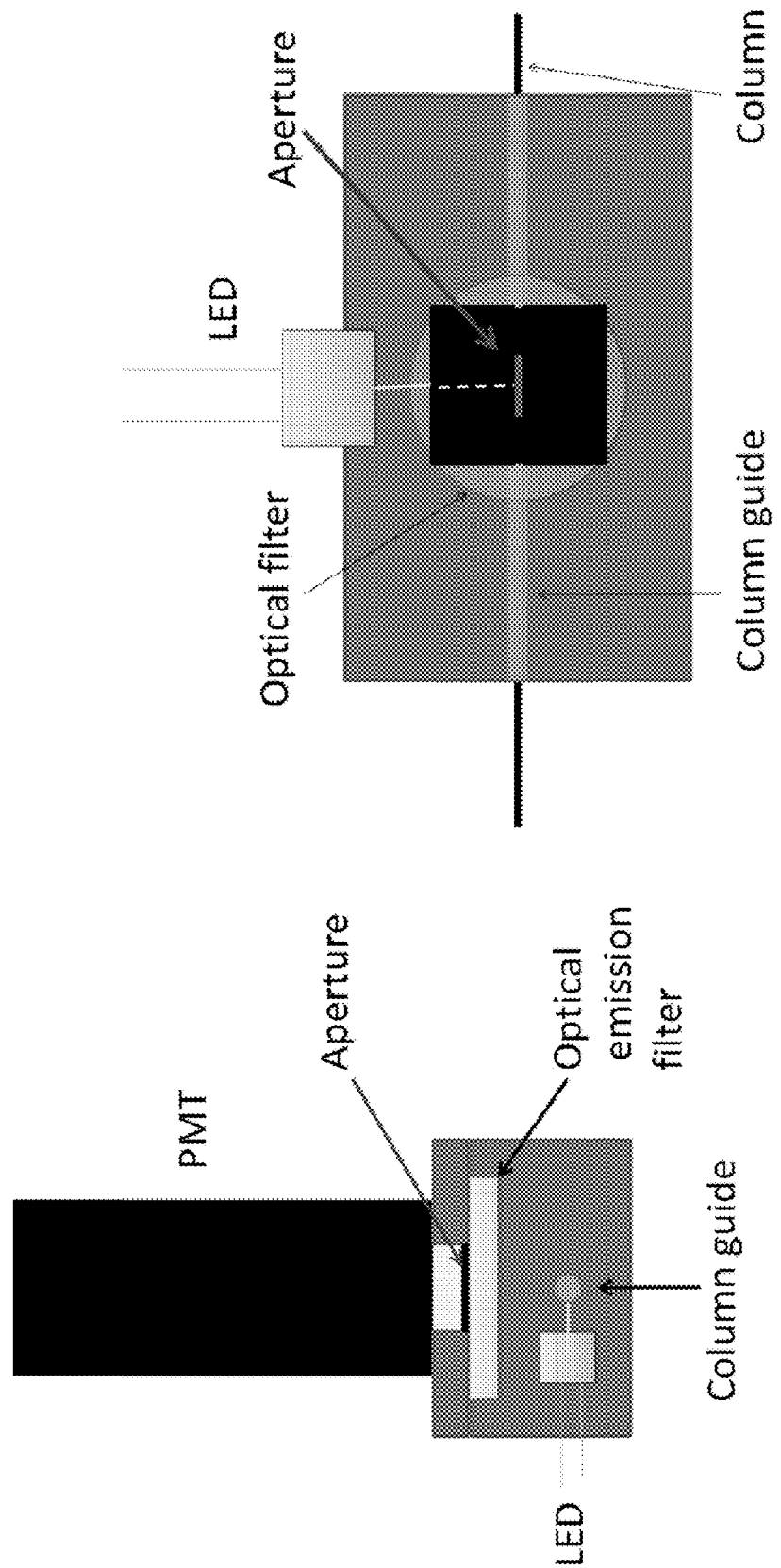
FIG. 8A and FIG. 8B illustrate optical detectors that can be used in conjunction with the above integrated detection apparatuses.

Both optical and C4D detection have been used with open and packed capillary columns. FIG. 8A shows fluorescence detector design. Fluorescence is excited by a light source such as an LED, a laser diode, or is brought in through an optical fiber in the horizontal plane that is mechanically moved along the column. The distance between the light source and the capillary is kept to a minimum: the light however is admitted through an aperture. The fluorescence is read, after a suitable optical filter to remove the stray excitation radiation, by a miniature photomultiplier tube in the vertical plane. The apparatus of the invention may be not only used with fluorescent (or fluorescently tagged analytes), but also in a new form of indirect fluorescence detection that has been widely used in thin layer chromatography (TLC). The stationary phase in this case may be doped with an inorganic phosphor that glows under 254 nm or 365 nm radiation. When any analyte appears in the window that absorbs at this wavelength, the observed fluorescence decreases. This is similar to current practice of TLC, where analytes appears as dark spots/bands on a glowing background when thin layer separation is carried out on a suitably phosphor-doped separation media. This technique has not, until now been used in columnar chromatography because the analyte is detected in solution that elutes from the column, the ability to detect the analyte on and along the column itself makes this approach now suitable for columnar separations.

Figure 8B:
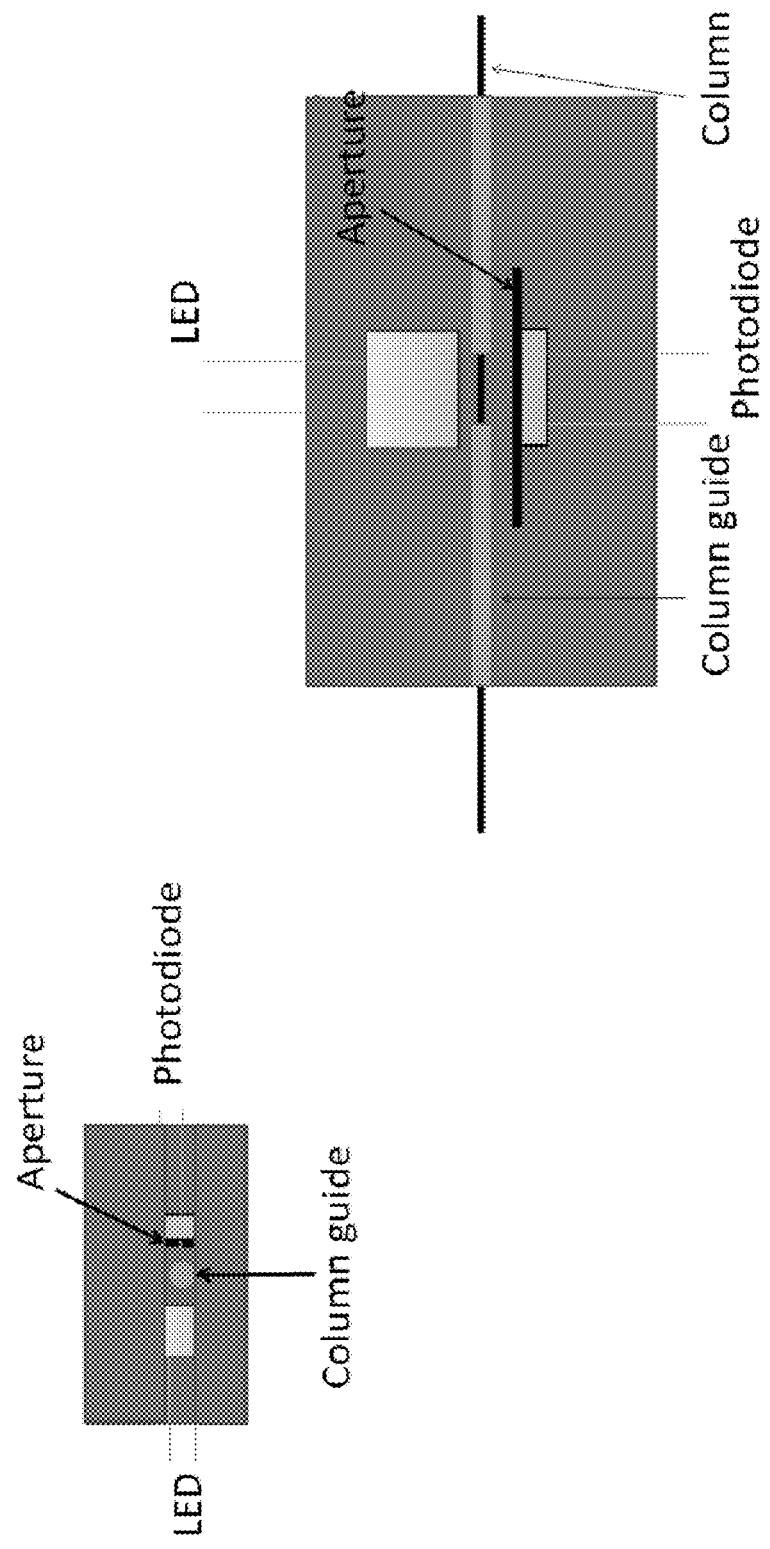

The absorbance detector is constructed independently or in the same body as the fluorescence detector. The photodetector used in various embodiments of the apparatus of the invention is a photodiode (e.g., Siemens BPW34) or a photodiode-op-amp combination (e.g., Texas Advanced Optical Systems TSL257) that is placed on the opposite side of the light source through an appropriate spatial aperture, as shown in FIG. 8B. Alternatively, designs with ball lenses may be used to couple light in and out of the capillary.

Figure 9:
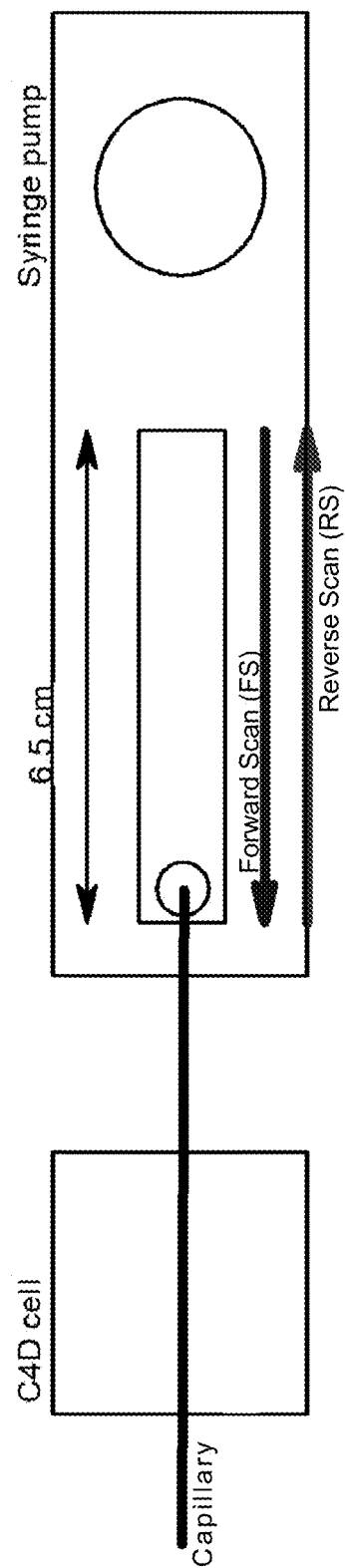
FIG. 9 illustrates an exemplary admittance detector apparatus in accordance with the present invention.

In other embodiments, the apparatus may be provided with an admittance detector and configured such that one of the separation conduit and the admittance detector move relative to the other in order to scan a length or partial lengths of the separation conduit to detect analyte moving through the length of the separation conduit. For example, the apparatus of FIG. 9 includes a capillary that moves relative to a C4D cell. In particular, the capillary may be moved by a syringe pump in forward and reverse scan directions. In the illustrated configuration, a Kloehn syringe pump was utilized to move the capillary a monitored length of 6.5 cm at a moving velocity of 1.4 mm/sec (1000 steps/sec) through an AD7746 based C4D detector cell including a pair of stainless steel tubes having a 0.54 mm I.D. and a 2.1 mm length with 1.0 mm distance. One will appreciate that other suitable configurations and dimensions may be used in accordance with the present invention.

Figure 10:
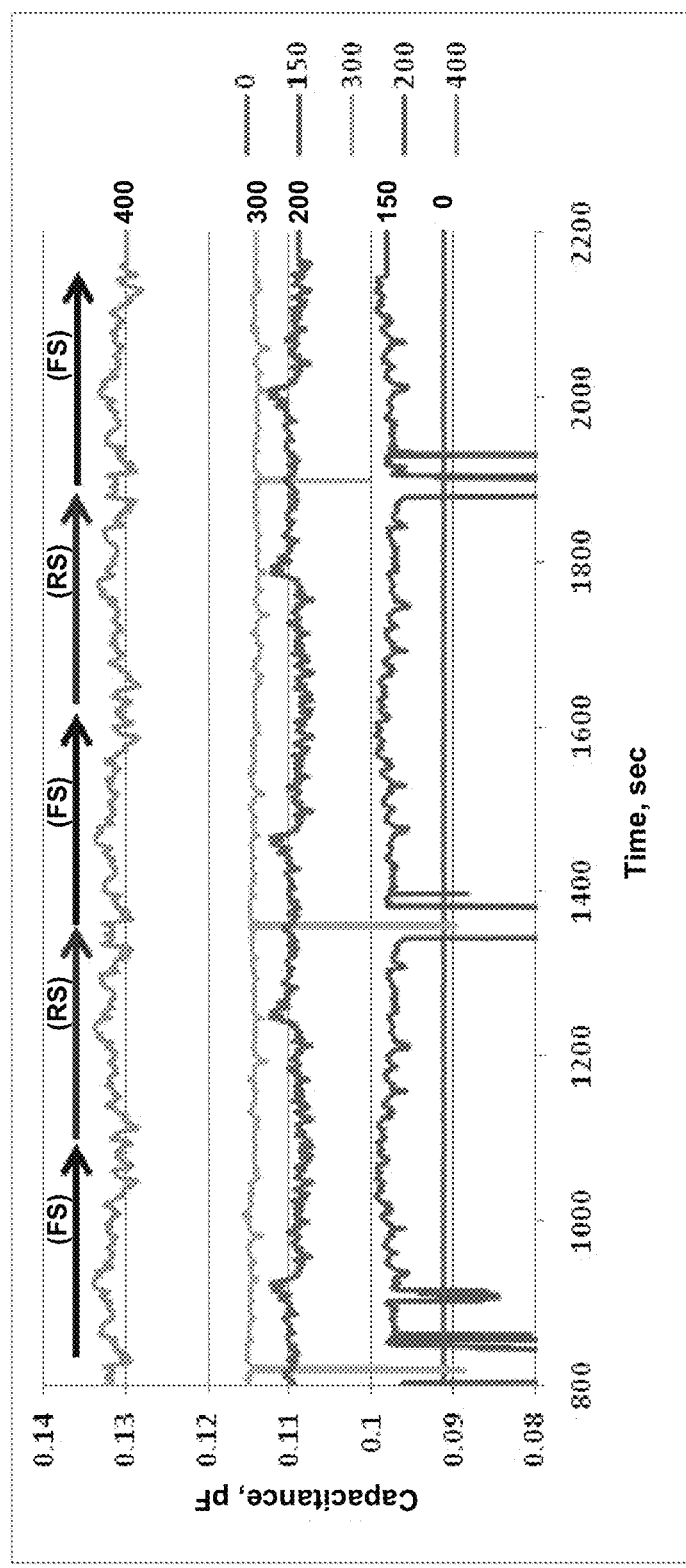
FIG. 10 illustrates scans of the admittance detector of FIG. 9 along a separation conduit.

The illustrated configuration was used to analyze fused silica capillaries having various thicknesses of an ionic liquid (IL), for example, a tricationic IL inside a NaCl treated column. The analysis results are shown in FIG. 10.

The following References, to the extent that they provide exemplary procedural or other details supplementary to those set forth above, are specifically incorporated by reference:

(1) David G. Gelderloos, Kathy L. Rowlen, and John W. Birks, *Whole Column Detection Chromatography: Computer Simulations*, Anal. Chem. 1986, 58, 900-903.

(2) E. E. Brumbaugh, and G. K. Ackers, *Molecular Sieve Studies of Interacting Protein Systems, III. Measurement of Solute Partitioning by Direct Ultraviolet Scanning of Columns*, J. Biol. Chem., 1968, 243, 6315-6324.

(3) Kathy L. Rowlen, Kenneth A. Duell, James P. Avery, and John W. Birks, *Whole Column Detection: Application to High-Performance Liquid Chromatography*, Anal. Chem., 1989, 61, 2624-2630.

(4) Jiaqi Wu, and Janusz Pawliszyn, *Universal Detection for Capillary Isoelectric Focusing Without Mobilization Using a Concentration Gradient Imaging System*, Anal. Chem. 1992, 64, 224-227.

(5) Jiaqi Wu, and Janusz Pawliszyn, *Application Of Capillary Isoelectric Focusing With Absorption Imaging Detection To The Analysis Of Proteins*, J. Chromatogr. B. Biomed. Appl., 1994, 657, 327-332.

(6) Stephen C. Beale, and Sara Jane Sudmeier, *Spatial-Scanning Laser Fluorescence Capillary Electrophoresis*, Anal. Chem. 1995, 67, 3367-3371.

(7) Jan Preisler, and Edward S. Yeung, *Characterization of Nonbonded Poly(ethylene oxide) Coating for Capillary Electrophoresis via Continuous Monitoring of Electroosmotic Flow*, Anal. Chem. 1996, 68, 2885-2889.

(8) Xing-Zheng Wu, Jiaqi Wu, and Janusz Pawliszyn, *Whole-Column-Imaging Detection for Capillary Isoelectric Focusing and Capillary Electrophoresis*, LCGC Mag. 2001, 19(5), 527-545.

(9) Xiaobing Xi, and Edward S. Yeung, *Axial-Beam On-Column Absorption Detection for Open Tubular Capillary Liquid Chromatography*, Anal. Chem., 1990, 62, 1580-1585.

(10) Akira Wada, Makoto Harada, and Tetsuo Okada, *Kinetic Monitoring of Electrophoretically Induced Solute Reaction by Axial Absorption Detection with Liquid-Core Waveguide*, Anal. Chem., 2006, 78, 4709-4712.

(11) P. K. Dasgupta, Z. Genfa, J. Z. Li, C. B. Boring, S. Jambunathan, and R. Al-Horr, *Luminescence Detection With a Liquid Core Waveguide*, Anal. Chem. 1999, 71, 1400-1407.

(12) Tim Dallas, and Purnendu K. Dasgupta, *Light at the End of the Tunnel: Recent Analytical Applications of Liquid Core Waveguides*, TrAC: Trends Anal. Chem., 2004, 23, 385-392.

(13) Jose A. Olivares, Peter C. Stark, and Paul Jackson, *Liquid Core Waveguide for Full Imaging of Electrophoretic Separations*, Anal. Chem. 2002, 74, 2008-2013

(14) Zhen Liu, and Janusz Pawliszyn, *Applications of Capillary Isoelectric Focusing With Liquid-Core Waveguide Laser-Induced Fluorescence Whole-Column Imaging Detection*, Analytical Biochemistry, 2003, 336, 94-101.

(15) Xing-Zheng Wu, Tiemin Huang, Zhen Liu, and Janusz Pawliszyn, *Whole-Column Imaging-Detection Techniques And Their Analytical Applications*, TrAC: Trends Anal. Chem. 2005, 24, 369-382.

(16) Shu-Hui Lin, Tiing Yu, Alf Sheu, Der-Jyh Yang, and Su-Cheng Pai, *Peak Crossover in High-Performance Liquid Chromatography Elution Monitored Using Whole-column Detection*, Journal of Chromatography A, 2008, 1201, 128-131.

(17) Jose A. Fracassi da Silva, and Claudimir L. do Lago, *An Oscillometric Detector for Capillary Electrophoresis*, Anal. Chem. 1998, 70, 4339-4343.

(18) P. Kuban, and P. C. Hauser, *Contactless Conductivity Detection For Analytical Techniques: Developments From 2010 To 2012*, Electrophoresis, 2013, 34, 55-69.

(19) Damian Connolly, Leon P. Barron, Eoin Gillespie, and Brett Paull, *The Use of Contactless Conductivity for the On-Column Characterisation and Visualisation of Packing Homogeneity and Band Broadening in Capillary LC*, Chromatographia, 2009, 70, 915-920.

(20) Eoin Gillespie, Damian Connolly, Mirek Macka, Peter Hauser, and Brett Paull, *Development of a Contactless Conductivity Detector Cell for 1.6 mm O.D. (1/16th inch) HPLC Tubing and Micro-Bore Columns With On-Column Detection*, Analyst, 2008, 133, 1104-1110.

(21) Damian Connolly, Patrick Floris, Pavel N. Nesterenko, and B. Paull, *Non-Invasive Characterization of Stationary Phases in Capillary Flow Systems Using Scanning Capacitively Coupled Contactless Conductivity Detection ($sC^4D$)*, TrAC: Trends in Analytical Chemistry, 2010, 29, 870-884.

(22) Aine Moyna, Damian Connolly, Ekaterina Nesterenko, Pavel N. Nesterenko, and Brett Paull, *Iminodiacetic Acid Functionalised Organopolymer Monoliths: Application to the Separation of Metal Cations by Capillary High-Performance Chelation Ion Chromatography*, Anal. Bioanal. Chem., 2013, 405, 2207-2217.

(23) A. F. Kadjo, and P. K. Dasgupta, *Tutorial: Simulating Chromatography with Microsoft Excel Macros*, Anal. Chim. Acta, 2013, 773, 1-8.

The foregoing descriptions of specific exemplary embodiments of the present invention have been presented for purposes of illustration and description. They are not intended to be exhaustive or to limit the invention to the precise forms disclosed, and obviously many modifications and variations are possible in light of the above teachings. The exemplary embodiments were chosen and described in order to explain certain principles of the invention and their practical application, to thereby enable others skilled in the art to make and utilize various exemplary embodiments of the present invention, as well as various alternatives and modifications thereof. It is intended that the scope of the invention be defined by the Claims appended hereto and their equivalents.

What is claimed is:

1. An apparatus for real time detection of elution of one or more analytes comprising:
   a separation conduit;
   an integrated detector including an excitation source and a sensor, both located immediately adjacent to the separation conduit, wherein the integrated detector is configured to move along a length of the separation conduit; and
   a driver moving the integrated detector along the length of the separation conduit;
   wherein the integrated detector scans the separation conduit and detects analyte as it moves through the separation conduit.

2. The apparatus of claim 1, wherein the separation conduit is a chromatography column.

3. The apparatus of claim 1, further comprising:
   a stationary base, wherein the separation conduit is mounted on the base;
   a carriage movably supported on the base and supporting the integrated detector, wherein the carriage is configured to move the integrated detector along the length of the separation conduit;
   wherein the driver moves the carriage and the integrated detector along the length of the separation conduit.

4. The apparatus of claim 3, further comprising a linear slide moveably supporting the carriage on the base.

5. The apparatus of claim 1, wherein the integrated detector is a conductance detector including electrodes positioned immediately outside of the separation conduit.

6. The apparatus of claim 1, wherein the integrated detector is a capacitance detector including electrodes positioned immediately outside of the separation conduit.

7. The apparatus of claim 1, wherein the integrated detector is an admittance detector.

8. The apparatus of claim 1, wherein the integrated detector is a capacitively coupled contactless conductivity detection (C4D) detector.

9. The apparatus of claim 1, wherein the integrated detector includes an excitation electrode and a pickup electrode disposed on opposing sides of a grounded planar electrode.

10. The apparatus of claim 9, wherein the excitation and pickup electrodes extend parallel to the separation conduit and the grounded planar electrode is disposed substantially perpendicular to the separation conduit.

11. The apparatus of claim 1, wherein the driver is a stepper motor.

12. The apparatus of claim 3, further comprising an optical detector mounted on the carriage and located adjacent to the separation conduit.

13. The apparatus of claim 12, wherein the optical detector includes an absorbance detector and/or a fluorescence detector.

14. The apparatus of claim 12, wherein the integrated detector and the optical detector are mounted in the same body.

15. A method for detecting elution of one or more analytes in real time, the method comprising:
- injecting an analyte sample through a separation conduit, the analyte sample containing an analyte within an eluent or background electrolyte; and
- repeatedly scanning the analyte sample as it moves through the conduit by moving an integrated detector along the length of the separation conduit;
- wherein time and space dependent data obtained from successive scans of the analyte sample is stored, and wherein the data is used to represent successive scans of the analyte sample.

16. The method of claim 15, wherein the repeatedly scanning step is accomplished by scanning as the detector moves in a forward direction along the length of the separation conduit.

17. The method of claim 16, wherein the repeatedly scanning step is accomplished by scanning as the detector moves in both forward and return directions along the length of the separation conduit.

18. The method of claim 16, wherein the repeatedly scanning step is accomplished by successively scanning respective portions of the length of the separation conduit.

19. The method of claim 15, wherein the separation conduit is a chromatography column.

20. The method of claim 15, wherein the integrated detector detects the analyte within the separation conduit by capacitively coupled contactless conductivity detection (C4D).

21. The method of claim 15, wherein the moving of the integrated detector is performed using a stepper motor.

22. The method of claim 15, wherein the method further comprising:
- prescanning the separation conduit prior to injecting the analyte sample, wherein the prescanning scans the eluent or background electrolyte flowing through the separation conduit without the analyte in order to determine a baseline run;
- wherein time and space dependent data obtained from the scan of the baseline run is stored and subtracted from each successive scan when similar scans are performed with an analyte sample injected.

23. The method of claim 15, wherein the method further comprising:
- injecting a calibration sample through the separation conduit, wherein the calibration sample is blank;
- scanning the calibration sample as it moves through the separation conduit by moving the integrated detector along the separation conduit;
- wherein time and space dependent data obtained from the scan of the calibration sample is stored and subtracted from each successive scan of the analyte sample.

24. The method of claim 15, wherein the separation conduit includes a stationary phase doped with an inorganic phosphor and a window, the method further comprising measuring a decrease in fluorescence when the analyte is in the window.

25. An apparatus for real time detection of elution of one or more analytes comprising:
- a separation conduit;
- an admittance detector located immediately adjacent to the separation conduit, wherein one of the separation conduit and the admittance detector are configured to move relative to the other of the separation conduit and the admittance detector;
- a driver configured to move the admittance detector back and forth along the length of the separation conduit;
- wherein the admittance detector scans a length of the separation conduit and detects analyte as it moves through the length of the separation conduit.

26. The apparatus of claim 25, wherein the separation conduit is a chromatography column.

27. The apparatus of claim 25, wherein the admittance detector includes electrodes positioned immediately outside of the separation conduit.

28. The apparatus of claim 25, wherein the admittance detector is a capacitively coupled contactless conductivity detection (C4D) detector.

29. The apparatus of claim 25, wherein the admittance detector includes an excitation electrode and a pickup electrode disposed on opposing sides of a grounded planar electrode, and wherein the excitation and pickup electrodes extend parallel to the separation conduit and the grounded planar electrode is disposed substantially perpendicular to the separation conduit.

* * * * *